(12) United States Patent
Ranu

(10) Patent No.: US 6,184,449 B1
(45) Date of Patent: Feb. 6, 2001

(54) 1-AMINOCYCLOPROPANE-1-CARBOXYLATE SYNTHASE GENES FROM ROSA TO CONTROL ETHYLENE LEVELS IN ROSES

(75) Inventor: Rajinder S Ranu, Fort Collins, CO (US)

(73) Assignee: Tagawa Greenhouses, Inc., Brighton, CO (US)

( * ) Notice: Under 35 U.S.C. 154(b), the term of this patent shall be extended for 0 days.

(21) Appl. No.: 09/171,482

(22) PCT Filed: Sep. 30, 1997

(86) PCT No.: PCT/US97/17644

§ 371 Date: Oct. 19, 1998

§ 102(e) Date: Oct. 19, 1998

(87) PCT Pub. No.: WO98/14465

PCT Pub. Date: Apr. 9, 1998

Related U.S. Application Data

(63) Continuation-in-part of application No. 08/724,194, filed on Oct. 1, 1996, now Pat. No. 5,824,875.

(51) Int. Cl.[7] ............... A01H 5/00; C12N 5/14; C12N 15/29; C12N 15/52; C12N 15/82
(52) U.S. Cl. ............... 800/323; 435/320.1; 435/419; 536/23.2; 536/23.6; 800/283; 800/286
(58) Field of Search .................. 435/69.1, 419, 435/320.1, 468; 536/23.2, 23.6; 800/278, 283, 286, 287, 298, 323

(56) References Cited

U.S. PATENT DOCUMENTS

| | | | |
|---|---|---|---|
| 4,237,224 | 12/1980 | Cohen et al. | 435/68 |
| 4,468,464 | 8/1984 | Cohen et al. | 435/317 |
| 4,740,463 | 4/1988 | Weinberg et al. | 435/172.3 |
| 4,740,470 | 4/1988 | Cohen et al. | 435/172.3 |
| 4,782,022 | 11/1988 | Puhler et al. | 435/172.3 |
| 4,801,540 | 1/1989 | Hiatt et al. | 435/172.3 |
| 4,962,028 | 10/1990 | Bedbrook et al. | 435/172.3 |
| 5,107,065 | 4/1992 | Shewmaker et al. | 800/205 |
| 5,123,951 | 6/1992 | See et al. | 71/86 |
| 5,208,149 | 5/1993 | Inouye | 435/91 |
| 5,272,065 | 12/1993 | Inouye et al. | 435/91.1 |
| 5,378,619 | 1/1995 | Rogers | 435/172.3 |
| 5,416,250 | 5/1995 | Ferro et al. | 800/205 |
| 5,565,347 | 10/1996 | Fillatti et al. | 435/172.3 |
| 5,674,731 | 10/1997 | Lin et al. | 435/240.4 |
| 5,689,055 | 11/1997 | Meyerowitz et al. | 800/205 |
| 5,723,766 | 3/1998 | Theologis et al. | 800/205 |
| 5,759,829 | 7/1998 | Shewmaker et al. | 435/172.3 |
| 5,824,868 | 10/1998 | Meyerowitz et al. | 800/205 |
| 5,824,875 | * 10/1998 | Ranu | 800/205 |

OTHER PUBLICATIONS

Oeller PW, et al. "Reversible inhibition of tomato fruit senescence by antisense RNA." Science 254:437–439, Oct. 1991.*

Firoozabady E, et al. "Regeneration of transgenic rose (Rosa hybrida) plants from embryogenic tissue." Bio/Technol. 12: 609–613, Oct. 1991.*

"The Role of Ethylene in Regulating Growth of Deepwater Rice," H. Kende, S. Hoffmann–Benning and M. Sauter MSU–DOE Plant Research Laboratory, Michigan State University, East Lansing, MI, USA, J.C.Pech et al. (eds.), Cellular and Molecular Aspects of the Plant Hormone Ethylene, 329–334, 1993, Kluwer Academic Publishers.

"Temporal and Spatial Regulation of 1–Aminocyclopropane–1Carboxylate Oxidase in the Pollination–Induced Senescence of Orchid Flowers", Jeanette A. Nadeau, Xian Sheng Zhang, Helen Nair, and Sharman D. O'Neill*, Division of Biological Science, Section of Plant Biology, University of California at Davis, Davis, CA, Plant Physiol. (1993) 103:31–9.

"A Flower Senescence–Related mRNA from Carnation Shares Sequence Similarity with Fruit Ripening–Related mRNAs Involved in Ethylene Biosynthesis," Hong Wang and William R. Woodson, Department of Horticulture, Purdue University, West Lafayette, IN, Plant Physiol (1991) 1000–1001.

"Ethylene and Flower Senescence," Michael S. Reid & Men–Jen Wu, Department of Environmental Horticulture, University of California, Davis, CA, Plant Growth Regulation II: 37–43, 1992.

"Cloning and Characterization of the cDNA encoding 1–Aminocyclopropane–1–Carboxylate (ACC) Synthase from Pelargonium Hortorum–sincerity", Jianguo Fan, Dong Wang and Rajinder Ranu, Department of Plant Pathology and Weed Science, Colorado State University, Fort Collins, RNA 2368, The FASEB Journal, Apr. 30, 1996, vol. 10, No. 6.

"Expression of Two ACC Synthase mRNAs In Carnation Flower Parts During Aging and Following Treatment With Ethylene," Hans Henskens, Dianne Somhorst and Ernest J. Woltering, Agrotechnological Research Institute (ATO–DLO) P.O. Box 17, 6700 AA Wageningen, The Netherlands, J.C. Pech et al. (eds), Cellular and Molecular Aspects of the Plant Hormone Ethylene, 323–324, 1993 Kluwer Academic Publishers.

(List continued on next page.)

*Primary Examiner*—Amy J. Nelson
(74) *Attorney, Agent, or Firm*—Santangelo Law Offices, P.C.

(57) ABSTRACT

A gene which encodes an ACC synthase is isolated from rose plants, specifically Rosa (cardinal red). This gene is modified for expression in transgenic plants. Isolation of high quality mRNA for gene isolation is achieved through use and adaptation of a 2-butoxyethanol precipitation technique using large amount of initial tissue in order to achieve critical mass for precipitation.

13 Claims, 5 Drawing Sheets

OTHER PUBLICATIONS

"Nucleotide Sequence Of A cDNA Encoding 1–Aminocyclopropane–1–Carboxylate Oxidase from Senescing Orchid Petals," Jeanette A. Nadeau and Sharman D. O'Neill, Division of Biological Science, Section of Plant Biology, University of California, Davis, CA., Plant Physiol, (1995) 108: 833–834.

"Nucleotide Sequence of a cDNA Encoding the Ethylene–Forming Enzyme from Petunia Corollas," Hong Wang and William R. Woodson, Department of Horticulture, Purdue University, West Lafayette, IN, Plant Physiol, (1992), 100, 535–536.

Abeles, F.B., et al. 1992, *Ethylene in Plant Biology*. Eds. Abeles, F.B., Morgan, P.W. and Saltveit, M.E. Academic Press, New York, pp 1–13.

Abeles, F.B., et. al. 1992, *Ethylene in Plant Biology*. Eds. Abeles, F.B., Morgan, P.W. and Saltveit, M.E. Academic Press, New York, pp 285–291.

Yang, S. F., et al, 1984, "Ethylene Biosynthesis and its Regulation in Higher Plants", *Annu. Rev. Plant Physiol*. 35:155–189.

Nell, T.A., 1993, "Use and Care Advice" White J.W., ed., Geranium IV. *The Grower's Manual,* Edition Four, Ball Publishing, Geneva, IL pp 171–172.

Chomczynski, P., et al, 1987, "Single–Step Method of RNA Isolation by Acid Guanidinium Thiocyanate–Phenol–Chloroform Extraction", *Analytical Biochemistry,* 162, 156–159.

Manning, K., 1991, "Isolation of Nucleic Acids from Plants by Differential Solvent Precipitation", *Analytical Biochemistry* 195, 45–50.

Mullis, K.B., et al, 1987, "Specific Synthesis of DNA in Vitro via a Polymerase–Catalyzed Chain Reaction", *Methods in Enzymology,* 155:335–350.

Sanger, F., et al, 1977, "DNA sequencing with chain–terminating inhibitors", *Proc. Natl. Acad. Sci. USA* 74:5463–5467.

Ranu, R.S., 1995, "DNA Sequencing with ▲ Taq® Polymerase", *Biotechniques* 18:390–395.

Ranu, R.S., et al, 1996, "In Vitro Translation of the Full–Length RNA Transcript of Figwort Mosaic Virus (Caulimovirus)", *Gene Expression,* vol. 5:143–153.

Ranu, R.S., et al, 1979, "Regulation of Protein Synthesis in Rabbit Reticulocyte Lysates: Preparation of Efficient Protein Synthesis Lysates andthe Purification and Characterization of the Heme–Regulated Translational Inhibitory Protein Kinase", *Methods in Enzymology* vol. 60:459–484.

Rottmann, W.H., et al, 1991, 1–Aminocyclopropane–1–Carboxylate Synthase in Tomato is Encoded by a Multigene Family Whose Transcription is Induced During Furit and Floral Senescence, *Journal of Molecular Biology,* 222, 937–961.

Van Der Straeten, D., et al, 1990, "Cloning and sequence of two different cDNAs encoding 1–aminocyclopropane–1–carboxylate synthase in tomato", *Proceeding of the National Academy of Sciences,* 87:4859–4863.

Zarembinski, T.I., et al, 1994, "Ethylene biosynthesis and action: a case of conservation", *Plant Molecular Biology,* 26:1579–1597.

Park, K.Y., et al, 1992, "Molecular cloning of an 1–aminocyclopropane–1–carboxylate synthase from senescing carnation flower petals", *Plant Molecular Biology,* 18:377–386.

Schlagnhaufer, C.D., et al, 1995, "Molecular cloning of an ozone–induced 1–aminocyclopropane–1–carboxylate synthase cDNA and its relationship with a loss of rbcS in potato (*Solanum tuberosum* L.)", *Plant Molecular Biology,* 28:93–103.

Wang, T.W. and Arteca, R.N., 1995, "Identification and Characterization of cDNAs Encoding Ethylene Biosynthetic Enzymes from Pelargonium x hortorum cv Snow Mass Leaves", *Plant Physiology,* 109:627–636.

Sato, T., et al, 1989, "Cloning the mRNA encoding 1–aminocyclopropane–1–carboxylate synthase, the key enzyme for ethylene biosynthesis in plants", *Proceedings of the National Academy of Sciences,* 86:6621–6625.

Nakajima, N., et al, 1990, "Molecular Cloning and Sequence of a Complementary DNA Encoding 1–Aminocyclopropane–1–carboxylate Synthase Induced by Tissue Wounding", *Plant Cell Physiology,* 31:1021–1029.

Dong, J.G., et al, 1991, "Cloning of a cDNA encoding 1–aminocyclopropane–1–carboxylate synthase and expression of its mRNA in ripening apple fruit", *Planta,* 185:38–45.

Olson, D.C., et al, 1991, "Differential expression of two genes for 1–aminocyclopropane–1–carboxylate synthase in tomato fruits", *Proceedings of National Academy of Sciences,* 88:5340–5344.

Smith, C.J.S., et al, 1991, " Antisense RNA inhibition of polygalacturonase gene expression in transgenic tomatoes", *Nature,* 334:724–726.

Yip, W.K., et al, 1990, "Differential accumulation of transcripts for four tomato 1–aminocyclopropane–1–carboxylate synthase homologs under various conditions", *Proceedings of the National Academy of Sciences,* 89:2475–2479.

Botella, J.R., et al, 1992, "Identification and characterization of a full–length cDNA encoding for an auxin–induced 1–aminocyclopropane–1–carboxylate synthase from etiolated mung bean hypocotyl segments and expression of its mRNA in response to indole–3–acetic acid", *Plant Molecular Biology,* 20:425–436.

Liang, X., et al, 1992, "The 1–aminocyclopropane–1–carboxylate synthase gene family of *Arabidopsis thaliana"*, *Proceedings of the National Academy of Sciences,* 89:11046–11050.

John, M.E., "An efficient method for isolation of RNA and DNA from plants containing polyphenolics", Nucleic Acids Research 20:2381, 1992.

Logemann, J., et al, 1987, "Improved Method for the Isolation of RNA from Plant Tissues", Anal Biochem 163: 16–20.

Kende, H., et al, 1993, "Ethylene Biosynthesis", *Annual Review of Plant Physiology, Plant Mol. Biol.,* 44:283–307.

Murray, A.J. 1993, "Expression of EFE Antisense RNA in Tomato Causes Retardation of Leaf Senescense and Most Fruit Ripening Characteristics", *Cellular and Molecular Aspects of the Plant Hormone Ethylene,* 327–328.

Michael, M.Z., et al, 1993, "Cloning of Ethylene Biosynthetic Genes Involved in Petal Senescence of Carnation and Petunia, and their Antisense Expression in Transgenic Plants", *Cellular and Molecular Aspects of the Plant Hormone Ethylene,* 298–303.

Gray, J.E., et al, 1993, "Altered Gene Expression, Leaf Senescence, and Fruit Ripening by Inhibiting Ethylene Synthesis with EFE–Antisense Genes", *Cellular and Molecular Aspects of the Plant Hormone Ethylene,* 82–89.

Theologis, A., et al 1993, "Modifying Fruit Ripening By Supressing Gene Expression", *Cellular and Molecular Aspects of the Plant Hormone Ethylene,* 19–23.

Hamilton, AJ et al 1990, "Antisense Gene that Inhibits Synthesis of the Hormone Ethylene in Transgenic Plants", *Nature,* 346:284–287.

Karlin, Samuel and Altschul, Stephen, "Methods For Assessing The Statistical Significance Of Molecular Sequence Features By Using General Scoring Schemes", Proc. Natl. Acad. Sci. USA vol. 87, pp 2264–2268, Mar. 1990.

Karlin, Samuel and Altschul, Stephen, "Applications and Statistcs For Multiple High–Scoring Segments In Molecular Sequences", Proc. Natl. Acad. Sci. USA vol. 90, pp 5873–5877, Mar. 1993.

Altschul, Stephen F., et al, "Gapped BLAST and PSI–BLAST: A New Generation Of Protein Database Search Programs", Nucleic Acids Research, 1997, vol. 25, No. 17, pp. 3389–3402.

Satot, Takahide, et al, "The 1–Aminocyclopropane–1–carboxylate Synthase of Cucurbita", The Journal of Biological Commistry, vol. 286, No. 6, Feb. 5, pp. 3752–3759 (1991).

Altschul, S.F. (1997) "Sequence Comparison and Alignment," in "DNA and Protein Sequence Analysis" (M.J. Bishop & C. J. Rawlings, eds.) pp. 137–167, IRL Press, Oxford.

T.F. Smith and M.S. Waterman, "Indentification of Common Molecular Subsequences," J. Molecular Biology 147:195–197 (1981).

M.S. Waterman and M. Eggert, "A New Algorithm for Best Subsequence Alignments With Application to tRNA–rRNA Comparison," J. Molecular Biology 197:723–728 (1987).

* cited by examiner

METHODNINE

①

S-ADENOSYL-METHIONINE
(ADOMET)

② (catalyzed by
ACC synthase)

1-AMINOCYCLOPROPANE-1-CARBOXYLATE
(ACC)

③

ETHYLENE cDNA synthesis flow chart

GCCTTGGCTTTC CTCCCTTCGCTTTCTTCTTCTTCTTCTTCATCATCGTACTCTCCGACG

ACCCGAAACCCC ACCGCGACCCGGCCCGGATGTCTCCAATATGACCCGGACCCGAGACGA

AGACCGGCGACC CAGCAGCAGCAGCAGCGGCGGCGGAGGAGGCGCCGATGAGAGTTATAG

TCCCTCTACAAG GCGTGGTTCAAGGCAGAGGAGGACTCGTTCTCGGCTCCGTCATACCAT

GCGCGCTCTTCT ATTTCCTCCAGCTTTATCATGAAACGTCACCGTTCCAACTCCAACCCG

CCGACTCCGCCG CCTTCTCCGGACTCGGACTCGGACCACCACCCCGCCGGGCAGTTGGTG

GAAGTTCCGGTT CTGCCCCGGTCGATGTCGAGGTCCCATCTCTCTCCGAGGAACCCGGGT

CCGGTACATGTC TCGGGTCGGGCCAATTCGGTTTTGAAAGGCGGTGAGCCGCCGTATTAT

GTCGGCTTGAGG AAGGTGGCGGAGGATCCGTACGACGAGTTGGGTAACCCGGATGGGGTT

ATTCAGCTGGGT TTGGATGAAAACAAGTTAGCTTTGGACTTGGTTCGAGATTGGCTACTG

GAGAATGCAAAG GATGCAATACTGGGTGGTGAGGAGCTTGGGATTAGTGGGATTGCTTGT

TACCAGCCTTCT GATGGTTTAATGGAGCTCAAACTGGCTGTGGCAGGATTCATGTCTAAG

GCCATCGGAAAT TCAGTTACGTACAACCCCTCACAAATTGTATTGACAGCTGGTGCAACC

CCTGCAATTGAG ATTCTAAGCTTCTGCCTAGCAGACAGTGGAAACGCATTTCTCGTTCCG

GCACCATATTAC CCTGGTTTGGACAGAGATGTGAAGTGGCGAACTGGAGTGGAGATAATA

CCTGTTCCATGC CGCAGTGCTGACAAATTCAATTTAAGTATAACTGCACTTGATCGAGCA

TTCAACCAGGCA AAGAAACGTGGTGTAAAAGTTCGTGGGATTATAATTTCAAATCCTTCA

AATCCTGGTGGC AGTTACTTACTCGTGAATCACTTTACAACCTTCTGGACTTTGCCCGA

GAGAAGAACATT CATATAATCTCAAATGAATTGTTTGCTGGATCCACGTATGGAAGTGAA

GAGTTTGTTAGC ATGGCAGAAATCGTTGATTTGGAAGATCTCGACCAGAACAGAGTGCAT

ATAGTATATGGC ATATCGAAGATCTCTCACTTCCAGGTTTCAGGGTGGGTGCCATCTAC

TCCTTTAACAAG AATGTCTTGACTGCTGCTAAAAAGTTGACAAGGTTCTCTTCTATCTCC

GCCCCATCCCAA CGGTTGCTTATCTCTATGCTTTCAGACACCAAATTTATGCATAAGTTC

ATCGAGATTAAC AGAGAAAGGCTCCGTGGAATGTATCTTAGATTTGTGACAGGATGAAG

Fig. 3a

CAATTGGGCATTGAGTGCACAAAGAGCAATGGGGGTTTCTACTGTTGGGCAGACTTGAGT

GGGTTAATTCGCT CTTACAGTGAGAAAGGGGAGCTTGAGCTCTGGGATAGGTTGTTGAAT

GTAGGTAAGCTCAATGTTACTCCTGGATCTTCTTGTCATTGTATTGAACCGGGATGGTTC

CGGTTTTGTTTTACGACGTTGACTGAAAAAGATATCCCTGTTGTTATAGAACGAATTCGG

AATATTGCCGAAACATGTAAATCACACAGTTGAAATGTTCGTTCATTCTACTCAAAAAAA

AAA

Fig. 3b

MKRHRSNSNPPTPPPSPDSDSDHHPAGQLVEVPVLPRSMSRSHLSPRNPGPVHV

SGRANSVLKGGEPPYYVGLRKVAEDPYDELGNPDGVIQLGLDENKLALDLVRDW

LLENAKDAILGGEELGISGIACYQPSDGLMELKLAVAGFMSKAIGNSVTYNPSQ

IVLTAGATPAIEILSFCLADSGNAFLVPAPYYPGLDRDVKWRTGVEIIPVPCRS

ADKFNLSITALDRAFNQAKKRGVKVRGIIISNPSNPGGSLLTRESLYNLLDFAR

EKNIHIISNELFAGSTYGSEEFVSMAEIVDLEDLDQNRVHIVYGISKDLSLPGF

RVGAIYSFNKNVLTAAKKLTRFSSISAPSQRLLISMLSDTKFMHKFIEINRERL

RGMYLRFVTGLKQLGIECTKSNGGFYCWADLSGLIRSYSEKGELELWDRLLNVG

KLNVTPGSSCHCIEPGWFRFCFTTLTEKDIPVVIERIRNIAETCKSHS

Fig. 4

1-AMINOCYCLOPROPANE-1-CARBOXYLATE SYNTHASE GENES FROM ROSA TO CONTROL ETHYLENE LEVELS IN ROSES

This application is a 371 of PCT application PCT/US97/17644 filed on Sep. 30, 1997 which is a continuation-in-part of U.S. application Ser. No. 08/724,194 filed on Oct. 1, 1996, now issued as a U.S. Pat. No. 5,824,875.

BACKGROUND OF THE INVENTION

This invention relates to the field of compositions and methods for inhibiting the enzyme 1-aminocyclopropane-1-carboxylate (ACC) synthase in rose thereby prolonging the shelf-life of cut flowers as well as reducing leaf yellowing and petal abscission during shipping and storage.

A variety of factors cause wilting and natural abscission in flowers, particularly after a cutting of the plant or when flowers have been removed from the plant. Such factors include increased oxygen levels, wounding, chemical stress, and the plant's own production of ethylene. Of these factors, the plant's production of ethylene, has been shown to play a key role in natural senescence, the degenerative process which generally leads to controlled cell death in plants, but also in the degradation of flowers after they have been cut.

Ethylene, in all higher plants, is important to plant growth and development from seed germination, seedling growth to flowering and senescence (Abeles, F. B. et al. (1992), In: Ethylene in Plant Biology. Eds. Abeles, F. B. et al., Academic Press, New York, pp 285–291 and 1–13; Yang, S. F. et al. (1984), Annu. Rev Plant Physiol:35, 155–189). Ethylene production in plants can also be associated with trauma induced by mechanical wounding, chemicals, stress (such as produced by temperature and water amount variations), and by disease. Hormones can also stimulate ethylene production. Such ethylene, also sometimes called "stress ethylene", can be an important factor in storage effectiveness for plants. Moreover, exposure of plant tissue to a small amount of ethylene often may be associated with increased production of ethylene by other adjacent plants. This autocatalytic effect may be often associated with losses in marketability of plant material during storage and transportation (Abeles et al., supra; Yang et al., supra).

The ethylene biosynthetic pathway in plants was established by Adams and Yang (Adams D. O., et al., (1979) Proc. Nat'l Acad Sci USA 76: 170–174)). The first step involves the formation of S-adenosyl-L-methionine (AdoMet) from methionine by S-adenosyl-L-methionine synthetase. AdoMet is then converted into 1-aminocyclopropane-1-carboxylate (ACC), the direct precursor of ethylene in higher plants. This conversion is catalyzed by ACC synthase (S-adenosyl-L-methionine methyl thioadenosine-lyase, EC4.4.1.14), the rate limiting step in the ethylene biosynthetic pathway. (See also Kionka C., et al., (1984) Planta 162:226–235; Amrhein N. et al., (1981) Naturwissenschaften 68: 619–620; Hoffman N. E., et al., (1982) Biochem Biophys Res Commun 104:765–770).

Knowledge of the biosynthetic pathway for ethylene formation has been fundamental in developing strategies for inhibiting ethylene production in plants. One approach has been to use chemical inhibitors to inhibit the synthesis or activity of ethylene, two of the most common being aminoethoxyvinylglycine and aminooxyacetic acid (Rando, R. R., 1974, Science, 185, 320–324 and in Ethylene in Plant Biology, (Abeles, F. B., et al., eds. Academic Press, p. 285)). However, chemical methods find limited use because such methods are expensive and the beneficial effect they provide is generally only short-lived.

A second approach has been to over express ACC deaminase, an enzyme which metabolizes ACC, thereby eliminating an intermediate in the biosynthesis of ethylene (Klee, et al., (1991) Cell 3: 1187–1193) (See also Theologis, A., et al. (1993), Cellular and Molecular Aspects of the Plant Hormone Ethylene, p. 19–23). Because ACC deaminase is a bacterial enzyme, it is heterologous, and thus, external to the plant. Thus, it is unlikely that this approach will yield a modification that will be stable from generation to generation.

Yet another approach involves attempts to genetically inhibit the production of the enzymes involved in the biosynthesis of ethylene or to inhibit the biosynthesis of the enzymes directly. This approach has the advantage of not only altering the way the plant itself functions irrespective of external factors but also of presenting a system which reproduces itself, that is, the altered plant's progeny will have the same altered properties for generations to come.

Initial efforts to better understand the enzymes which catalyze the reactions in the biosynthesis of ethylene have involved the identification and characterization of the genes encoding for AdoMet synthetase, ACC synthase, and ACC oxidase (See also Kende H., 1993, Annu Rev Plant Physiol Mol Biol 44:283–307). Some of the genes encoding for ACC synthase have been identified for a number of plants. For instance, ACC synthase sequences have been identified for zucchini (Sato T., et al., (1989) Proc. Natl Acad Sci USA 86:6621–6625), winter squash (Nakajima, N., et al., (1990) Plant Cell Physiol 31:1021–1029), tomato (Van Der Straeten, D., et al., (1990) Proc Natl Acad Sci USA 87:4859–4863); (Rottmann, W. H., et al., (1991) J Mol Biol 222:937–961), apple (Dong, J. G., et al., (1991) Planta 185:38–45), mung bean (Botella, J. R., et al., (1992a) Plant Mol Biol 20:425–436; Botella, J. R., et al., (1993) Gene 123: 249–253; Botella, J. R., et al., (1992b) Plant Mol Biol 18: 793–797); Kim, W. T., et al., (1992) Plant Physiol 98:465–471), carnation (Park, K. Y., et al., (1992) Plant Mol. Biol., 18, 377–386), Arabidopsis thaliana (Liang, X., et al., (1992) Proc Natl Acad Sci USA 89:11046–11050; Van Der Staeten, D., et al., (1992) Proc Natl Acad Sci USA 89:9969–9973), tobacco (Bailey, B. A., et al., (1992) Plant Physiol 100: 1615–1616), rice (Zarembinski, T. I., et al., (1993) Mol Biol Cell 4: 363–373), mustard (Wen, C. M., et al., (1993) Plant Physiol 103:1019–1020), orchid (O'Neill, S. D., et al., (1993) Plant Cell 5: 419–432), broccoli (Pogson, B. J., et al., (1995) Plant Physiol 108:651–657), and potato (Schlagnhaufer, C. D., et al.. (1995) Plant Mol. Biol. 28:93–103).

That ACC synthase is involved in the ethylene pathway is confirmed by the fact that increased levels of ACC synthase mRNA correlate with an increased activity of ACC synthase in plants during fruit ripening and flower senescence. Similar correlation is also observed in response to exogenous signals caused either by wounding or due to treatment with hormones such as auxin, cytokinin and ethylene. Interestingly, the expression of different classes of ACC synthase occurs from a variety of signals in many plants, e.g. four different ACC synthase genes have been shown to be differentially expressed in tomato fruit, cell cultures, and hypocotyls during ripening, wounding, and auxin treatment (Olson, D. C., et al (1991) Proc. Natl. Acad. Sci. USA 88:5340–5344; and Yip, W. K., (1992) Proc. Natl. Acad. Sci. USA 89:2475–2479). Differential expression of two ACC synthase genes has also been observed in winter squash during wounding or by auxin (Nakajima, et al. (1990) Plant Cell Physiol, 31; 1021–29 and (1991) Plant Cell Physiol, 32; 1153–63). Similar differential regulation of expression ACC synthase genes takes place in carnation flowers by wounding or during senescence (Park, K. Y., et al., (1992) *Plant Mol. Biol.*, 18, 377–386). The evolution of ACC synthase genes into a multigene family that responds differentially during plant development or in response to stimuli external to the plant (Rottmann, W. H., et al., (1991) *J Mol Biol* 222:937–961) may be a reflection of the importance of ethylene in plants. (See also Slater, A., et al., (1985) Plant Mol Biol 5:137–147). (Smith, C. J. S., et al., (1986) Planta 168; 94–100 and Smith, C. J. S., et al. (1988) Nature 334;724–26). (Hamilton, A. J., et al., (1990) Nature 346:284–286; Köck, M., et al., (1991) Plant Mol Biol 17:141–142).

The discovery of the foregoing and of other properties has lead to an understanding that it may be desirable to attempt to genetically alter the production of ethylene in plants. This approach, however, may be considered in some ways delicate. Elimination of ethylene is not a desired result as in many instances it will kill the plant. Modulation of ethylene—at the appropriate times—is the critical goal, not elimination of it entirely. This has been attempted at least two points in the pathway: the production of ACC by ACC synthase, and the oxidation of ACC by a different enzyme, ACC oxidase. Because the ACC synthase approach can permit stable modulation and not only total elimination of ethylene, it is a preferred technique. To date, however, successful reduction of the production of ethylene through an alteration at the ACC synthase step in the pathway has only been accomplished in one plant, tomato (Oeller, et al. (1991) *Science* 254:437–39). In spite of the seemingly simple conceptual nature of this goal, the actual accomplishment of an alteration of the ethylene biosynthetic pathway through the ACC synthase technique has remained elusive. This is particularly true for the rose plant, perhaps due to the fact that the identification of full length genes can be difficult for plants. As discussed later, this may, in part, be due to the fact that isolation of full length or high quality RNA has been deemed "notoriously difficult" for plants. (John, M. E., Nucleic Acids Research 20:2381, 1992, and Logemann, J. et al, Anal Biochem 163, 16–20, 1987).

Efforts by others highlight some of the difficulty involved. Recently, Arteca's laboratory (Wang, T. W. et al., (1995) *Plant Physiol.* 109:627–636) studied two cDNA molecules encoding ACC synthase from a white flower variety of a flowering geranium plant (*Pelargonium x hortorum* cv Snow Mass Leaves). As their publication explained (perhaps after the fact), these researchers tried to identify and characterize two clones, GAC-1 and GAC-2. In spite of their efforts, they were only able to completely identify one of those cDNA gene sequences, GAC-1. Their study examined the expression of these ACC synthase genes in different plant parts of the geranium and in response to stress induced by osmotic changes (sorbitol) or metal ions ($CuCl_2$). It also evaluated the effects of ethylene on auxin 2,4-D induction in geranium leaves. The study indicated that GAC-1 expression was induced only by stress, whereas expression of GAC-2 appeared to be developmentally regulated. Furthermore, these authors speculated about possible future "transfer of antisense GAC-1, GAC-2 . . . into Pelargonium tissues through the Agrobacterium transformation or particle bombardment." This confirms a desire in the art for an ACC synthase approach to altering ethylene production in such plants. In spite of this desire, however, the isolation and identification of some, if not all, the ACC synthase gene sequences—for geranium remained elusive. In similar fashion, rose as well has remained elusive.

Although several plant ACC synthase genes have been identified and sequenced, the current invention describes ACC synthase gene sequences which were previously unknown and which are not believed to have been easily discoverable. As mentioned, one factor which may have militated against an expectation of successfully cloning a plant gene is the particular difficulty in obtaining high-quality and full-length RNA from plants. Indeed, this process has been characterized as "notoriously difficult" by at least more than one practitioner of the art (John, M. E., *Nucleic Acids Res.* 20:2381, 1992 and Logemann, J., et al, *Anal Biochem* 163, 16–20, 1987)). While this proved to be true for the present inventor, these difficulties were overcome by assessing a new approach to the RNA isolation process. The current inventor, after finding traditional RNA isolation methods to be ineffective, was forced to develop a non-traditional approach described herein. Basically, even though those of ordinary skill in the art had long desired to identify some gene to manipulate to alter the production of ethylene in some plants, in this case, they failed to realize that the problem lay in the need for a better isolation process. Even though the implementing technology for this process had long been available, those in the art apparently failed to realize how to use that technology to achieve the results now described. To some extent they simply may not have defined the problem, preventing the achievement the goals sought. Their efforts may properly be characterized as having taught away from the direction taken by the present inventor and, thus, the results achieved here should be considered unexpected.

Difficulties in isolating full-length mRNA in the specific case of geranium and rose are also further reflected by the fact that one of the sequences encoding ACC synthase in a geranium isolated by the current inventor (clone pPHSacc49), though it may bear some similarity to portions of the clone termed GAC-2 by Wang et al., supra, (which, in any case, may have been discovered after the making of the present invention) is actually considerably longer than GAC-2. This highlights the difficulty in successfully isolating a full-length mRNA molecule using standard RNA isolation procedures in certain plant materials including roses. However, the high quality RNA (as defined below) isolated by the current inventor is evidenced by the fact that full length cDNA clones were obtained in a different plant, and all of them could be successfully expressed in an in vitro expression system. In each case, full length ACC synthase (enzyme) protein is synthesized in vitro. In contrast, even later publications by Arteca's group do not describe the actual in vitro expression of any of the isolated DNA clones. In fact the cDNA for the GAC-2 gene was never isolated. Rather, only a partial sequence was merely deduced from the sequence of genomic clones.

This is significant because it highlights the difficulty in isolating and thereby identifying full length ACC synthase genes. Those of ordinary skill in the art had faced the same challenge. Derivation of DNA encoding ACC synthase from a genomic clone rarely is successful, and therefore, simply would not necessarily provide a reasonable expectation of success to one of ordinary skill. Only by utilizing a new and different approach did the present invention successfully identify not only one but several full length ACC synthase gene sequences from the geranium plant. The same technique applies to the identification of the ACC synthase gene sequence from the rose plant. Basically, it was this high quality library containing full length cDNA clones which allowed the present inventor to successfully achieve direct cloning of ACC synthase cDNA. The prior art did not discover these sequences because the genes did not exist in the available libraries. It was this new approach which overcame the problems faced, but not solved, by others and resulted in the extraordinary successes described herein. The extraordinary success of the present invention— a nearly one hundred fold increase in positive identifications is a consequence of the new technique for RNA isolation and cDNA identification, and not the result of analogous knowledge gained from the efforts of others. Mere comparison to other genes in the same or different plants did not and could not have yielded the successes described here. The existence of the cDNAs of interest in the library was the governing factor. Thus, even with a viable identification process, successful identification of the rose ACC synthase gene, let alone the actual alteration of the plants themselves by means of this knowledge, would not have been likely.

Additionally, it should be understood that knowledge of the full length sequence of a gene from other plants simply does not necessarily lead one to the sequences of the homologous genes in the rose plants. First, as mentioned earlier, the genes encoding ACC synthase have evolved into a multigene system in some cases. There appears to be no single gene, but rather a family of genes in most cases. Thus, knowledge of one gene in one plant species is not certain to lead to one (or several) homologous or analogous genes in another plant species. Second, because known ACC synthase genes are typically so diverse in their nucleotide sequences, knowledge of one would not lead a person of ordinary skill in the art to an expectation of success in isolating the ACC synthase gene from rose.

Antisense technology is a well known approach to create a plant that produces less of a selected protein. Through this technology, a plant is altered by introducing a foreign DNA sequence that encodes an mRNA product complementary to part or all of the plant's "sense" mRNA encoding the protein. The presence of antisense RNA inhibits RNA function within a cell (and whole organism). Antisense RNA can bind in a highly specific manner to its complementary sense RNA resulting in blockade in processing and/or translation of the sense mRNA. Antisense RNA may also disrupt interactions between sense mRNA and sequence-specific RNA binding proteins. Antisense technology may be employed to inhibit the synthesis of an enzyme involved in ethylene biosynthesis. The genes identified by the current inventor and disclosed herein have been used for the conception and implementation of antisense sequences specific for ACC synthase mRNA. Introduction of DNA encoding such antisense RNA sequences into a rose plant is highly probable to result in a plant which stably produces less ethylene.

The incorporation of antisense RNA in plants as a means to inhibit the synthesis of enzymes has been described by various investigators. Rothstein, et al. (1987) *Proc. Natl. Acad. Sci. U.S.A.* 84: 8439, found that antisense RNA inhibited nopaline synthase (nos) in tobacco. Smith, C. J. S., et al. (1988) *Nature* 334: 724, reported that antisense RNA inhibited polygalacturonase in tomato. Others have used antisense RNA to inhibit the synthesis of enzymes involved in ethylene formation. Oeller, P. W., et al., (1991) *Science* 254: 437–439, expressed RNA antisense to ACC synthase in tomato plants. Others have expressed antisense RNA to a different ethylene forming enzyme (EFE), ACC oxidase, in carnation and tomato (Michael, M. Z., et al., 1993, In: Pech, J. C., et al., eds., *Cellular and Molecular Aspects of the Plant Hormone Ethylene* (Kluwer Academic Publishers, pp. 298–302); Hamilton, A. J., et al. (1990) *Nature* 346: 284–287; Gray, et al. (1993), in Pech, J. C., et al., supra, pp. 82–89; Murray, A. J., et al. (1993) in Pech, J. C., et a., supra,, pp. 327–328). The above work with antisense RNA may also be applicable to efforts to stably incorporate the sequences identified by the current inventor and their antisense sequences into a rose plant. Similarly, the success in expressing antisense RNA for ACC synthase in tomato plants may also be applicable (Oeller, et al., supra). It is noteworthy, and perhaps surprising, that neither of the foregoing disclosures have led to the long sought goal of stably altering ethylene production in rose plants. Hence, no altered rose plants expressing reduced levels of ethylene has been described. The incorporation of ACC synthase antisense DNA into a rose plant has remained elusive because the complete ACC gene sequences were not available prior to the present invention. The discoveries disclosed herein enable the production of an appropriately altered rose plant which will express ACC synthase antisense sequences and stably produce reduced levels of ethylene.

SUMMARY OF THE INVENTION

This invention is based on the discovery and cloning of multiple 1-amino cyclopropane-1-carboxylate (ACC) synthase cDNA molecules. In a rose, there is one molecule which represents the ACC synthase gene from Rosa (actually the cardinal red rose cultivar of the rosa genus). The nucleotide sequence and corresponding amino acid sequence for this gene is disclosed herein. Importantly, this is believed the first report of the full-length sequence for this gene, evidenced by the ability of the cDNAs to be expressed in an expression system.

The invention provides a method for genetic modification of rose plants to control their levels of ethylene. The newly discovered DNA sequences, fragments thereof, or combinations of such sequences or fragments, is introduced into a plant cell in reverse orientation to inhibit expression of ACC synthase, thereby reducing the levels of endogenous ethylene.

Using the above methods or plant-specific variants of them, transgenic plants are to be developed and monitored for growth and development. Those plants exhibiting prolonged shelf-life with respect to plant growth, flowering, and/or reduced yellowing of leaves due to reduction in levels of ethylene are to be selected and propagated as premier products with improved properties including reduced leaf yellowing and petal abscission during shipping and storage.

The present invention is directed to an isolated DNA molecule encoding an ACC synthase enzyme of a rose which DNA molecule hybridizes with pRoseKacc7 (SEQ ID NO: 1) or a functional derivative of the DNA molecule which hybridizes with SEQ ID NO: 1.

The isolated DNA molecule is preferably one with substantial sequence homology with a molecule selected from the molecule set out in SEQ ID NO: 1. In one embodiment, the isolated DNA molecule is that of SEQ ID NO: 1.

In another embodiment, the present invention provides an isolated protein encoded by a DNA molecule as described above, or a functional derivative thereof A preferred protein has an amino acid sequence of SEQ ID NO: 2 or is a functional derivative thereof.

Also provided herein is an antisense oligonucleotide or polynucleotide encoding an RNA molecule which is complementary to at least a portion of an RNA transcript of the DNA molecule described above, which RNA molecule hybridizes with the RNA transcript such that expression of the ACC synthase enzyme is altered.

The above antisense oligonucleotide or polynucleotide molecule can be full length or preferably has between six—or ten, twenty, or fifty—and 100 nucleotides.

The antisense oligonucleotide or polynucleotide may be complementary to at least a portion of one strand of the nucleotide sequence SEQ ID NO: 1 or may be complementary to at least a portion of an RNA sequence encoded by SEQ ID NO: 1. In one embodiment, the antisense oligonucleotide is complementary to at least a part of a 5' non-coding portion of one strand of the nucleotide sequence SEQ ID NO: 1.

An antisense oligonucleotide as described above may be complementary to at least a part of the nucleotide sequence SEQ ID NO: 1, which part is, for example, from nucleotides 1–50; nucleotides 51–100; nucleotides 101–150; nucleotides 151–200; nucleotides 201–250; nucleotides 251–300; 301–350; 351–400; 401–450; or 451–500; or any other such contiguous group up to nucleotide 500, 1000, or even to the end of the gene.

This invention is her directed to a vector useful for transformation of a rose plant cell, comprising:
 (a) an antisense oligonucleotide or polynucleotide as described above;
 (b) regulatory sequences required for expression of the oligonucleotide or polynucleotide in the cell.

The regulatory sequences comprise a promoter active in the cell, which may be an inducible promoter or preferably, a constitutive promoter. The vector preferably further comprise a polyadenylation signal.

In the above vector the promoter is preferably a heterologous promoter such as a viral promoter. A preferred viral promoter is the CaMV 35S promoter or a promoter homologous to CaMV35S.

In other embodiments, the promoter is selected from the group consisting of the SSU gene promoter, ribulose bisphosphate carboxylase promoter, chlorophyll a/b binding protein promoter, potato ST-LS1 gene promoter, soybean heat shock protein hsp17.5-E promoter, soybean heat shock protein hsp17.3-B promoter, phenylalanine ammonia-lyase promoter, petunia 5-enolpyruvylshikimate-3-phosphate synthase gene promoter, *Rhizobium meliloti* FIXD gene promoter and nopaline synthase promoter.

Also provided is a rose cell transformed with a vector as described above, a plantlet or mature rose plant generated from such a cell, or a plant part from such a plant.

The present invention is further directed to a method to alter expression of an ACC synthase enzyme in a rose cell, plant or a cutting thereof, comprising:
 (a) transforming either a rose cell or a plant with a vector according to any of the prior directions; and
 (b) allowing the antisense oligonucleotide or polynucleotide to be expressed and to hybridize with nucleic acid molecules in the cell, plant or cutting which encode the ACC synthase enzyme.

Also provided is a method of producing a rose plant having reduced ethylene production compared to an unmodified plant, comprising the steps of:
 (a) transforming a rose plant with a vector as above;
 (b) allowing the plant to grow to at least a plantlet stage;
 (c) testing the plant for ACC synthase enzymatic activity or ethylene production; and
 (d) selecting a plant having altered ACC synthase activity and/or altered ethylene production compared to an unmodified rose plant.

A rose plant produced as above, or progeny, hybrids, clones or plant parts thereof, preferably exhibits reduced ACC synthase expression and reduced ethylene production.

In another embodiment, the invention is directed to a method for producing either a rose or a rose variety (or line), characterized by reduced expression or activity of an ACC synthase enzyme and reduced ethylene production compared to an unmodified rose or rose variety, comprising producing a rose plant as above and selfing the plant to generate the variety.

Also provided is a method for producing a variant plant of a non-rose species, an ACC synthase gene of which is homologous to a rose ACC synthase gene, in which variant plant the ACC synthase expression is altered in comparison to an unmodified plant of the species, comprising:
 (a) identifying and isolating an ACC synthase gene of the species by hybridization with a sense DNA molecule as described above;
 (b) constructing a vector which comprises an antisense DNA sequence encoding at least a part of the gene identified in step (a) in an antisense orientation such that
  (i) an RNA transcript of the antisense DNA sequence is complementary to the part of the gene, and
  (ii) expression of the antisense DNA sequence alters expression of the ACC synthase gene;
 (c) transforming a cell of a plant of the species with the vector of step (b) to generate a transformed cell; and
 (d) regenerating a plant from the transformed cell of step (c), to produce the variant plant.

The above method is also used to produce a plant variety in a non-rose plant species characterized by reduced expression or activity of an ACC synthase enzyme and reduced ethylene production compared to a conventional variety of the species, comprising producing a variant plant as above, and selfing the plant to generate the variety.

This invention also provides a method for genetically altering a plant, preferably (but not necessarily) a plant of a low RNA species, comprising the steps of:
 (a) isolating mRNA of the plant using the 2-butoxyethanol precipitation technique wherein at least about 3–5 grams of plant tissue starting material is used to attain a critical mass amount of RNA for precipitation;
 (b) constructing a cDNA library from the isolated mRNA;
 (c) identifying and cloning a desired DNA sequence from the library;
 (d) genetically altering the cloned DNA sequence;
 (e) transforming cells of the plant or the plant directly with the altered DNA sequence; and
 (f) if done through a cell-based technique, reproducing a plant from the cells which plant expresses the altered DNA sequence,
thereby genetically altering the plant.

In the above method the plant is preferably a species of the genus Rosa. In the above method, the cloned DNA sequence preferably encodes ACC synthase. The cDNA in the above method is preferably selected from the group consisting of SEQ ID NO: 1.

The above method is used to produce a genetically altered rose plant, comprising the steps of:
 (a) isolating rose mRNA using a 2-butoxyethanol precipitation technique wherein at least about 3–5 grams of plant tissue starting material is used to attain a critical mass amount of RNA for precipitation;
 (b) constructing a cDNA library from the isolated mRNA;
 (c) identifying and cloning at least one DNA sequence from the library;
 (d) genetically altering the cloned DNA sequence;
 (e) transforming rose cells with the altered DNA sequence; and (f) regenerating the genetically altered rose plant from the cells, which plant expresses the altered DNA sequence.

The invention is further directed to a method of isolating plant mRNA, comprising the steps of:

(a) extracting nucleic acids from a sufficient amount of plant tissue starting material to attain a critical mass amount of RNA for precipitation;

(b) isolating RNA from the nucleic acids of step (a) using a 2-butoxyethanol precipitation technique;

(c) contacting the RNA with a binding partner for mRNA, for example oligo-dT or another molecule or entity which has the characteristics of binding specifically to mRNA with the exclusion of other forms of RNA or DNA. The binding partner may be immobilized on a solid phase or carrier; this yields immobilized mRNA; and (d) eluting the immobilized mRNA from the carrier by conventional elution methods, or obtaining bound mRNA, thereby isolating the mRNA from total RNA.

BRIEF DESCRIPTION OF THE DRAWINGS

FIGS. 3A–3B show the nucleotide sequence of the cDNA clone designated pRoseKacc7 (SEQ ID NO: 1). The following landmarks are indicated: the start ATG codon is in bold and underscored; the termination codon of the coding sequence (TGA) is in bold and double underscored.

FIG. 4 shows the deduced amino acid sequence (SEQ ID NO: 2) encoded by nucleotide sequence SEQ ID NO: 1.

DETAILED DESCRIPTION OF THE PREFERRED EMBODIMENTS

Figure 1:
FIG. 1 shows the ethylene biosynthetic pathway including the step catalyzed by ACC synthase.
Figure 1:
Figure 1:

The present inventor has isolated, cloned and identified a cDNA sequence encoding the enzyme ACC synthase in a rose plant (specifically from Rosa). This cDNA sequence corresponds to a gene which is important in the control of ethylene production. The DNA is expressed in any of a number of expression systems, including an in vitro expression system to yield a polypeptide product which preferably has ACC synthase enzymatic activity.

The cloned ACC synthase gene or fragments thereof, when introduced in reverse orientation (antisense) under control of a strong promoter (discussed below in detail), such as the cauliflower mosaic virus promoter CaMV35S, can be used to genetically modify a rose plant. Selected antisense sequences sharing sufficient homology to ACC synthase genes in other plants can be used to achieve similar genetic modification. One result of this modification is a reduction in the amount of translatable ACC synthase-encoding mRNA. As a consequence, the amount of ACC synthase produced in the plant cells is reduced, thereby reducing the rate of conversion of ACC to ethylene. This genetic modification can effect a permanent change in ethylene levels in the modified plant and be propagated in offspring plants by selfing or other reproductive schemes. Hence, the invention provides a plant modified as described herein as well as plants which, although modified in a different manner achieve similar results or utilize similar concepts as disclosed herein. The genetically altered plant is used to produce a new variety or line of plants wherein the alteration is stably transmitted from generation to generation.

The rose plant is an ethylene-sensitive flowering plant. A change in ethylene level may thus have a great impact on its commercial desirability. The present invention provides isolated ACC synthase genes obtained specifically from a rose for use in genetic modification preferably of rose plants. The full length DNA molecules described herein are unique to roses and vary significantly in sequence from ACC synthase DNA in any other unrelated plant species.

Because of such interspecies variation, to achieve stable genetic modification, it may be important that an ACC synthase gene or gene fragment (a) be obtained from the same species or (b) be a functional derivative of the DNA sequence native to the species. However, it is possible that a selected sequence from one plant genus or species may be employed using antisense technology in a different genus or species to achieve a useful effect such as that described here. The present invention thus provides for the first time the appropriate DNA sequences which may be used to achieve a stable genetic modification primarily of rose plants (and of other plants as well).

For the identification, in general, preparation of plasmid DNA, restriction enzyme digestion, agarose gel electrophoresis of DNA, Southern blots, Northern blots after separation of the RNA on a formaldehyde agarose gel, DNA ligation and bacterial transformation were carried out using conventional methods well-known in the art. See, for example, Sambrook, J. et al., *Molecular Cloning: A Laboratory Manual*, 2nd Edition, Cold Spring Harbor Press, Cold Spring Harbor, N.Y., 1989.

As used herein, the term "plant" refers to either a whole plant, a plant part, a plant cell, or a group of plant cells. The types of plants which can be used in the method of the invention generally includes the genus Rosa (roses) which can take up and express the DNA molecules of the present invention. It may include plants of a variety of ploidy levels, including haploid, diploid, tetraploid, and polyploid.

A "transgenic plant" is defined as a plant which is genetically modified in some way, including but not limited to a plant which has incorporated heterologous DNA or modified DNA or some portion of heterologous or homologous DNA into its genome. The altered genetic material may encode a protein, comprise a regulatory or control sequence, or may comprise an antisense sequence or encode an antisense RNA which is antisense to an endogenous DNA or mRNA sequence of the plant. A "transgene" or a "transgenic sequence" is defined as a foreign or atypical gene or partial sequence which has been incorporated into a transgenic plant.

As used in the present application, the term "substantial sequence homology" or "substantially homologous" is used to indicate that a nucleotide sequence (in the case of DNA or RNA) or an amino acid sequence (in the case of a protein or polypeptide) exhibits substantial functional or structural equivalence with another nucleotide or amino acid sequence. Any functional or structural differences between sequences having substantial sequence homology will be de minimis; that is, they will not affect the ability of the sequence to function as indicated in the desired application. Differences may also be simply due to inherent variations in codon usage among different species. Sequences that have substantial sequence homology with the sequences disclosed herein are usually "variants" of the disclosed sequence, such as mutations, but may also be synthetic sequences. Structural differences are considered de minimis if there is a significant amount of sequence overlap or similarity between two or more different sequences or if the different sequences exhibit similar physical characteristics even if the sequences differ in length or structure. Such characteristics include, for example, ability to hybridize under defined conditions, or, in the case of proteins, immunological crossreactivity, similar enzymatic activity, etc.

Additionally, two nucleotide sequences are substantially homologous if the sequences have at least 70 percent, more preferably 80 percent and most preferably 90 percent sequence similarity between them. Two amino acid sequences are substantially homologous if they have at least 50 percent, preferably 70 percent, and most preferably 90 percent similarity between the active portions of the polypeptides. Further the term "substantial sequence homology" should be understood to comprise any similarity which meets at least any default criteria of any model (as now readily ascertainable to those of ordinary skill in the art), or any permutation of the following criteria, each of which may also be separately specified as well to narrow the scope at any time.

A. Search Scoring Models, Parameters, and Costs
   (using any program model available, as applicable, including but not limited to those based upon the Smith-Waterman algorithm (with and without extensions or amendments by Gotoh or others), BLAST, PSI-BLAST, Gapped BLAST, or MPSRCH)
   Matches: +1, +3, or +5
   Mismatches: −1, −3, or −5
   Gap Existence Cost (per gap): −1, −6, −10, or −30
   Gap Size Cost (per residue): −1, −2, −3, −6, or −10
      (such that in some models a gap of length x with a gap existence cost of A and a gap size cost of B would result in a scoring reduction of A+Bx for each gap)

B. Lowest Percent Similarity Levels
   (defined as the above scoring divided by any of: the length of the sequence at issue, the length of the local portion of the sequence at issue, or the average length of the sequence at issue and the compared sequence)
      for Amino Acid Sequence Comparisons
         all percentages from 50% to 100% in 2% increments (based on either global similarities or local similarities)
      for Nucleotide Sequence Comparisons
         all percentages from 70% to 100% in 2% increments (based on either global similarities or local similarities)

The term "hybridization" as used herein is generally understood to mean hybridization at appropriate conditions of stringency as would be readily evident to those skilled in the art depending upon the nature of the probe sequence and target sequences. Conditions of hybridization and washing are well-known in the art, and the adjustment of conditions depending upon the desired stringency by varying incubation time and temperature and ionic strength of the solution are readily accomplished. See, for example, Sambrook, J., et al., *Molecular Cloning: A Laboratory Manual,* Second Edition, Cold Spring Harbor Press, Cold Spring Harbor, N.Y. (1989). The choice of conditions is dictated by the length of the sequences being hybridized, in particular the length of the probe sequence, the relative G-C content of the nucleic acid and the amount of mismatches to be permitted. Low stringency conditions are preferred when partial hybridization between strands that have lesser degrees of complementarity is desired. When perfect or near-perfect complementarity is desired, high stringency conditions are preferred. For typical high stringency conditions, the hybridization solution contains 6× SSC, 0.01M EDTA, 5× Denhardt's solution and 0.5% SDS. Hybridization is carried out at about 68° C. for 3–4 hours for fragments of cloned DNA and 12–16 hours for total eukaryotic DNA. For lower stringency, the temperature is reduced to about 12° C. below the melting temperature ($T_m$) of the duplex. The $T_m$ is known to be a function of G-C content and duplex length as well as the ionic strength of the solution.

By "functional derivative" of a nucleic acid (or poly- or oligonucleotide) is meant a "fragment," "variant," "homologue" or "analogue" of the gene or DNA sequence encoding ACC synthase, or in some way related to the production or use of ACC synthase, especially rose ACC synthase. A functional derivative may retain at least a portion of the function of the ACC synthase-encoding DNA which permits its utility in accordance with one embodiment of the present invention. Such function may include the ability to hybridize with native rose or homologous DNA from another plant which encodes ACC synthase or with an mRNA transcript thereof, or, in antisense orientation, to inhibit the transcription and/or translation of rose ACC synthase mRNA or the like.

A "fragment" of the gene or DNA sequence refers to any subset of the molecule, that is, a shorter polynucleotide- or oligonucleotide. A "variant" refers to a molecule substantially similar to either the entire gene or a fragment thereof, such as a nucleotide substitution variant having one or more substituted nucleotides but which maintains the ability to hybridize with the particular gene or to encode a mRNA transcript which hybridizes with the native DNA. A "homologue" refers to a fragment or variant sequence from a different plant genus or species. An "analogue" refers to a non-natural molecule substantially similar to or functioning in relation to either the entire molecule, the variant, or to a fragment thereof.

"Altered" expression" or an "alteration" of expression of a gene (most particularly of ACC synthase), as used herein, refers to any process or result whereby the normal expression of the gene, for example that occurring in an "unmodified" rose plant, defined as a known, conventional, naturally-occurring rose plant, is changed in some fashion. As intended herein, an alteration is a complete or preferably a partial reduction in the expression of ACC synthase, but may also include a change in the timing of expression, or another state wherein the expression of ACC synthase differs from that which would be most likely to occur naturally in an unmodified rose plant, variety or cultivar. A preferred alteration is one which results in a decrease in ethylene production by the plant compared to ethylene production in an unmodified plant.

In producing a genetically altered plant according to this invention, it is preferred to select individual plantlets or plants by the desired trait, generally reduced ACC synthesis expression and reduced ethylene production. Expression of ACC synthase can be measured by quantitating the amount of ACC synthase mRNA using conventional hybridization techniques. Alternatively, the amount of ACC synthase protein can be quantitated, for example in a conventional immunoassay method using a specific antibody such as those described herein. Finally, the ACC synthase enzymatic activity can be measured using biochemical methods as described in Kionka et al., supra; Amrhein et al., supra; or Hoffman N. E., et al., supra. Ethylene biosynthesis in the plantlet or plant can be quantitated using known methods Yang, S. F. et al. (1984), *Annu. Rev Plant Physiol:*35, 155–189); Abeles, F. B. et al eds, *Ethylene in Plant Biology,* Academic Press, New York, 1976 White, J. W., ed., *Geranium IV. The Growers Manual,* Edition Four, Ball Publishing, Geneva, Ill.

In order for a newly inserted gene or DNA sequence to be expressed, resulting in production of the protein which it encodes (or, in the case of antisense DNA, to be transcribed, resulting in an antisense RNA molecule), the proper regulatory signals should be present in the proper location with respect to the coding or antisense sequence. These regulatory signals may include a promoter region, a 5' non-translated leader sequence and a 3' polyadenylation sequence as well as enhancers and other known regulatory sequence. The promoter is a DNA sequence that directs the cellular machinery to transcribe the DNA to produce RNA. The promoter region influences the rate at which the mRNA product and, if the DNA encodes a protein, the resultant protein product, are made. The 3'-polyadenylation signal is a non-translated region that functions in plant cells to cause the addition of a polyadenylate stretch to the 3' end of the mRNA to stabilize it in the cytoplasm for subsequent translation.

A promoter DNA sequence is operably linked to a second DNA sequence and regulates its transcription. If the second DNA sequence encodes a protein, the promoter DNA sequence is said to be "operably linked" if it affects the transcription of the mRNA encoding the protein product from the second DNA sequence. A DNA sequence comprising a promoter is generally physically near the coding sequence in the same recombinant construct, though physical contiguity is not required. "Strong" promoters are able to direct RNA synthesis at higher rates than weaker promoters. Certain promoters direct RNA production at higher levels only in particular types of cells and tissues. Promoters that direct RNA production in many or all tissues of a plant without the need for "induction" by a specific inducer substance are called constitutive promoters. The operation of a constitutive promoter is relatively independent of the developmental stage of the cell in which it is contained and is most preferred for the present invention. An inducible promoter is one which, in response to the presence of an inducer, is activated. Hence, a coding sequence driven by an inducible promoter can be turned on or off by providing or withdrawing the inducer. A promoter may be homologous, derived from the same species as the coding sequence. Preferably, the promoter is heterologous, that is, derived from another species, or even from a virus.

Expression levels from a promoter which is useful for the present invention can be tested using conventional expression systems, for example, by measuring levels of a reporter gene product (protein or mRNA) in extracts of the leaves, stems, roots and flowers of a transgenic plant into which the promoter/reporter have been introduced.

Cauliflower mosaic virus (CaMV) is a double-stranded DNA plant virus. It contains two promoters responsible for the production of transcripts of 35S and 19S in size in infected plants (Guilley, H., et al, *Cell* 30:763 (1982)). The 35S promoter (CaMV35S) is one of the strongest constitutive heterologous promoters known in plants (Odell, et al., *Nature* 313:810–812 (1985); Jensen, et al., *Nature* 321:669–674 (1986); Jefferson, et al., *EMBO J.* 6:3901–3907 (1987); Kay, et al., *Science* 236:1299–1302 (1987); Sanders, et al., *Nucl. Acids Res.* 4:1543–1558 (1987)). Two different domains within the CaMV 35S promoter may differentially regulate expression of a coding sequence in different plant tissues (domain A, from nucleotides −90 to +8) vs. domain B from nucleotides −343 to −90), as described by Benfey, et al., 1989 *EMBO J* 8:2195–2202.) The CaMV35S promoter is active in isolated protoplasts (Fromm, M., et al., *Proc. Natl. Acad. Sci. USA* 82:5824 (1985)) and is expressed in all organs of various transgenic plants in the absence of any viral protein, making it widely used in plant genetic engineering.

Because of variability in the expression of genes driven by the CaMV35S promoter, (which may be either an intrinsic property of the promoter or a result of variability in the position at which CaMV35S promoter-driven DNA sequence is integrated into the genome of the transformed plant), CaMV35S may be particularly useful for effecting different degrees of altered gene expression by an antisense sequence which the promoter controls. Additional useful plant promoters in, for example, other caulimoviruses (a group of double-stranded DNA viruses to which the cauliflower mosaic virus belongs) have also been developed and are useful for similar applications. Two caulimoviruses distantly related to CaMV are the figwort mosaic virus (FMV) (Richins, et al., *Nucl. Acids Res.* 15:8451–8466 (1987)) and the carnation etched ring virus (CERV) (Hull, et al., *EMBO J* 5:3083–3090 (1986). The promoters of FMV and CERV which are homologues of the CaMV35S promoter are described in Rogers, U.S. Pat. No. 5,378,619. Any of the foregoing viral promoters, as well as other viral promoters which act as strong promoters for expression of plant DNA sequences in plant cells, may be used to drive the expression of the DNA molecules of the present invention.

Certain other strong plant promoters are also useful to direct the expression of the ACC synthase DNA (or antisense sequences) of the present invention. For example, the small subunit (SSU) of the enzyme ribulose-1,5-bisphosphate carboxylase (RuBPCase), the primary enzyme of the carbon fixation pathway in chloroplasts of plants of the C3 class is an example of a polypeptides known to be highly expressed in plants. A highly efficient SSU promoter DNA such as the promoter DNA from the SSU gene denominated SSU301 from Petunia (Bedbrook, et al., U.S. Pat. No. 4,962,028) may be used herein. The promoter may be used in the form of an isolated 5' fragment of the SSU gene, and preferably has the 3' end of the fragment modified to create a restriction site which permits ready fusions with the ACC synthase antisense DNA of the present invention. The promoter may be conveniently arranged to form an expression cassette comprising a 5' fragment (the promoter region of the SSU gene), a 3' fragment and a linker region connecting the two fragments. The fusion points between the 5' fragment and the linker region and between the 3' fragment and the linker region are preferably modified to create restriction sites which permit the antisense DNA of the present invention to be substituted for the linker so as to yield "chimeric" genes containing the complete proximal 5' and 3' regions of the SSU gene but none of the SSU coding sequence Other plant promoter enhancer/sequences which may be used in accordance with the present invention have been described in the following references: Coruzzi, et al., 1984, *EMBO J.* 3:1671–1680; Herrera-Estrella, et al., 1984, *Nature* 310:115–120; Apel, et al., 1978, *Eur. J. Became.* 85:581–588; Stiekema, et al., 1983, *Plant Physiol.* 72:717–724; Thompson, et al., 1983, *Planta* 158:487–500; Jones, et al., 1985, *EMBO J.* 4:2411–2418; Stockhaus, et al., 1989, *Plant Cell* 1:805–814; Gurley, et al., 1986, *Mol. Cell Biol.* 6:559–565; Landsmann, et al., 1988, *Mol. Gen. Genet.* 214:68–73; Bevan, et al., 1989, *EMBO J.* 8:1899–1906; Benfey, et al., 1989, *Science* 244:174–181.

Additionally, certain bacterial promoters have been observed to be expressed in plants, including the *Rhizobium meliloti* FIXD gene promoter (Puhler, et al., U.S. Pat. No. 4,782,022) and the nopaline synthase promoter (Ha, et al., 1989, *Nucl. Acids Res.* 17:215–224; An et al., 1988, *Plant*

*Physiol.* 88:547–552). Several promoter sequences, termed the rol A, B and C promoters, have been identified in *Agrobacterium rhizogenes* (Schmulling, et al., 1989, *Plant Cell* 1:665–670; Sugaya, et al., 1989, *Plant Cell Physiol.* 30:649–654).

To test the activity of a promoter, *E. coli* β-glucuronidase (GUS) coding sequence or a mutant Arabidopsis EPSP synthase gene which encodes an enzyme tolerant of glyphosate herbicides may be used as a reporter gene. Transformed plant cells or plants containing the GUS gene operably linked to the promoter being tested are assayed using a histological staining procedure to determine GUS activity in the transformed cells.

The present invention provides antisense oligonucleotides and polynucleotides complementary to the gene or genes encoding ACC synthase in a rose plant. Such antisense oligonucleotides, should be at least about six, ten, twenty, or fifty nucleotides in length to provide minimal specificity of hybridization, and may be complementary to one strand of DNA or to mRNA encoding ACC synthase (or to a portion thereof), or to flanking sequences in genomic DNA which are involved in regulating ACC synthase gene expression. The antisense oligonucleotide may be as large as about 100 nucleotides, an may extend in length up to and beyond the full coding sequence for which it is antisense. The oligonucleotides can be DNA or RNA or chimeric mixtures or derivatives or modified versions thereof, single-stranded or double-stranded.

The action of the antisense nucleotide may result in specific alteration, primarily inhibition, of ACC synthase gene expression in cells. For a general discussion of antisense, see: Alberts, B., et al., *MOLECULAR BIOLOGY OF THE CELL*, 2nd Ed., Garland Publishing, Inc., New York, N.Y. (1989), in particular, pages 195–196, which reference is hereby incorporated by reference.

The antisense oligonucleotide may be complementary to any portion of the ACC synthase encoding sequence. In one embodiment, the antisense oligonucleotide may be between about 6, 10, 20, or 50 and 100 nucleotides, and may be complementary to the initiation ATG codon and an upstream, non-coding translation initiation site of the ACC synthase sequence. For example, antisense nucleotides complementary primarily for non-coding sequence, are known to be effective inhibitors of the expression of genes encoding transcription factors (Branch, M. A., 1993 *Molec. Cell. Biol.* 13:4284–4290).

Preferred antisense oligonucleotides are complementary to a portion of the mRNA encoding ACC synthase. For instance, it is expected that by introducing a full length cDNA clone gene in an antisense orientation, successful alteration of gene expression will be most probable. Naturally, introduction of partial sequences, targeting to specific regions of the gene, and the like can be effective as well. An example of a preferred antisense oligonucleotide for a rose is a 50mer which is antisense to 50 nucleotides in the 5' half of an RNA transcript of an ACC-encoding cDNA (such as SEQ ID NO: 1), more preferably any stretch of 50 nucleotides in the first 500 nucleotides of the 5' part of the RNA transcript. For example, the antisense oligonucleotide can be antisense to nucleotides 1–50, 2–51, 3–52, 4–53, 5–54, etc., of the RNA transcript. Alternatively, the antisense oligonucleotide can be shorter for wither plant, for example a 30-mer, and be antisense to any 30 nucleotide stretch of the RNA transcript, preferably in the first 500 5' nucleotides.

As is readily discernible by one of ordinary skill in the art, the minimal amount of homology required by the present invention is that sufficient to result in sufficient complementarity to provide recognition of the specific target RNA and inhibition or reduction of its translation or function while not affecting function of other mRNA molecules and the expression of other genes. While the antisense oligonucleotides of the invention comprise sequences complementary to at least a portion of an RNA transcript of ACC synthase, absolute complementarity, although preferred, may not be required. A sequence "complementary to at least a portion of" another sequence, as referred to herein, may have sufficient complementarity to be able to hybridize with that of other sequences in vivo, perhaps forming a stable duplex. Naturally, the ability to hybridize may depend on both the degree of complementarity and the length of the antisense nucleic acid. Generally, the longer the hybridizing nucleic acid, the more base mismatches with the ACC synthase target sequence it may contain and still form a stable duplex. One skilled in the art can ascertain a tolerable degree of mismatch by use of standard procedures to determine the melting temperature of the hybridized complex as discussed above and other techniques.

The antisense RNA oligonucleotides may be generated intracellularly by transcription from exogenously introduced nucleic acid sequences. Thus, antisense RNA may be delivered to a cell by transformation or transfection or infection with a vector, such as a plasmid or a virus, into which is incorporated (a) DNA encoding the antisense RNA and operably linked thereto (b) the appropriate regulatory sequences, including a promoter, to express the antisense RNA in a target host cell (and whole plant). Within the cell the exogenous DNA or a portion thereof may be transcribed, producing an antisense RNA of the invention. Vectors can be plasmid, viral, or others known in the art which are used for replication and expression in plant cells. Expression of the sequence encoding the antisense RNA can be by any promoter known in the art to act in a plant, preferably rose cells. Such promoters can be inducible or preferably are constitutive as described above. Such a vector, preferably a plasmid, becomes chromosomally integrated such that it can be transcribed to produce the desired antisense RNA. Such plasmid or viral vectors can be constructed by recombinant DNA technology methods that are standard in the art.

An oligonucleotide, between about 6 and about 100 bases in length and complementary to the target sequence of ACC synthase, as described above may be prepared by chemical synthesis from mononucleotides or shorter oligonucleotides, or produced by recombinant means.

Basic procedures for constructing recombinant DNA and RNA molecules in accordance with the present invention are disclosed by Sambrook, J., et al., In: *Molecular Cloning: A Laboratory Manual,* Second Edition, Cold Spring Harbor Press, Cold Spring Harbor, N.Y. (1989), which reference is herein incorporated by reference. Oligonucleotide molecules having a strand which encodes antisense RNA complementary to an ACC synthase sequence can be prepared using procedures which are well known to those of ordinary skill in the art. Details regarding such procedures are described in: Belagaje, R., et al., *J. Biol. Chem.* 254:5765–5780 (1979); Maniatis, T., et al., In: *MOLECULAR MECHANISMS IN THE CONTROL OF GENE EXPRESSION,* Nierlich, D. P., et al., eds., Acad. Press, N.Y. (1976); Wu, R., et al., *Prog. Nucl. Acid Res. Molec. Biol.* 21:101–141 (1978); Khorana, H. G., *Science* 203:614–625 (1979)). Automated synthesizers may be used for DNA synthesis (such as are commercially available from Biosearch, Applied Biosystems, etc.).

Techniques of nucleic acid hybridization are disclosed by Sambrook et al. (supra), and by Haymes, B. D., et al., In:

NUCLEIC ACID HYBRIDIZATION, A PRACTICAL APPROACH, IRL Press, Washington, D.C. (1985)), which references are herein incorporated by reference.

The transgenic plants of the present invention may be prepared by DNA transformation using any method of transformation known in the art. These methods include transformation by direct infection or co-cultivation of plants, plant tissue or cells with *Agrobacterium tumefaciens* (Horsch, et al., *Science* 225:1229 (1985); Marton, *Cell Culture and Somatic Cell Genetic of Plants* 1:514–521 (1984)); Fry, et al., *Plant Cell Reports* 6:321–325 (1987); direct gene transfer into protoplasts or protoplast uptake (Paszkowski, et al., *EMBO J*. 12:2717 (1984); Loerz, et al., *Mol. & Gen. Genet.* 178:1199 (1985); electroporation Fromm, et al., *Nature* 319:719 (1986)); microprojectile or particle bombardment (Klein, et al., *Bio/Technology* 6:559–563 (1988)); injection into protoplasts cultured cells and tissues (Reich et al., *Bio/Technology*, 4:1001–1004 (1986)); or injection into meristematic tissues of seedlings and plants (De La Pena, et al, *Nature,* 325:274–276 (1987); Graves, et al., *Plant Mol. Biol.* 7:43–50 (1986); Hooykaas-Van Slogteren, et al., *Nature* 311:763–764 (1984); Grimsley, et al., *Bio/Technology* 6:185 (1988); and Grimsley, et al., *Nature* 325:177 (1988).

The *Agrobacterium tumefaciens* strain 208 carrying the disarmed pMP90RK plasmid can be used to achieve transformation. Used for plant transformations, the vector plasmid may be introduced into the Agrobacterium by the triparental conjugation system (Ditta, et al., (1980) *Proc. Natl. Acad. Sci. USA* 77:7347–7451) using the helper plasmid pRK2013. The vectors may be transferred to plant cells by the vir functions encoded by the disarmed pMP90RK Ti plasmid. The vector is opened at the pTiT37 right border sequence and the entire vector sequence is inserted into the host plant chromosome. The pMP9ORK Ti plasmid is probably not transferred to the plant cell but remains in the Agrobacterium.

Normally, regeneration will be involved in obtaining a whole plant from the transformation process. The term "regeneration" as used herein, means growing a whole plant from a plant cell, a group of plant cells, a plant part or a plant piece (e.g. from a protoplast, callus, tissue part, or explant, etc.) Plant regeneration from cultured protoplasts is described in Evans, et al., *Handbook of Plant Cell Cultures* 1:124–176 (MacMillan Publishing Co. New York 1983); Davey, M. R., *Protoplasts* (1983), Lecture Proceedings, pp.12–29, Birkhauser, Basel, 1983); P. J. Dale, ibid, at pp. 31–41, (Birkhauser, Basel 1983); and H. Binding, *Plant Protoplasts, pp.*21–73, CRC Press, Boca Raton, 1985).

Plant parts obtained from the regenerated plant in which expression of an ACC synthase gene has been altered, such as flowers, seeds, leaves, branches, fruit, and the like are included within the definition of "plant" as stated above, and are included within the scope of the invention. Progeny and variants and mutants of the regenerated plants are also included, especially if these parts comprise the introduced DNA sequences.

The present invention also provides ACC synthase proteins encoded for by the cDNA molecules described above. For roses, such proteins preferably have the amino acid sequence of SEQ ID NO: 2 as shown in FIG. 4. In each case, these proteins, or functional derivatives thereof, are preferably produced by recombinant methods optionally in combination with chemical methods.

A "functional derivative" of the ACC synthase protein is a "fragment," "variant," "analog," or "chemical derivative" of ACC synthase, which retains at least a portion of the function of the ACC synthase which permits its utility in accordance with the present invention. Such function includes enzymatic activity or immunological crossreactivity with an antibody specific for ACC synthase. A fragment of the ACC synthase protein refers to any subset of the molecule, that is, a shorter peptide. A variant refers to a molecule substantially similar to either the entire protein or a fragment thereof. Variant peptides may be conveniently prepared by direct chemical synthesis using methods well-known in the art. An "analog" of ACC synthase refers to a non-natural protein substantially similar to either the entire protein or a fragment thereof. A chemical derivative of ACC synthase contains additional chemical moieties not normally a part of the protein or peptide fragment thereof. Covalent modifications of an ACC synthase peptide are included within the scope of this invention. Such modifications may be introduced into the molecule by reacting targeted amino acid residues of the peptide with an organic derivatizing agent that is capable of reacting with selected side chains or terminal residues.

A protein or peptide according to the present invention may be produced by culturing a cell transformed with a DNA sequence of this invention, allowing the cell to synthesize the protein, and obtaining the protein from the culture medium if it is secreted, or if it is intracellular, obtaining it by extraction. In a preferred embodiment, the protein is produced in a cell free system, for example, as described by Ranu, R. S., et al, 1979, *Meth. Enzymol.* 60:459–484 and Ranu, R. S., et al, (1996) *Gene Expression* 5:143–153.

To produce an isolated, purified protein or peptide, the in vitro translation product or the cell or tissue extract from transformed plant cells or plant parts is subjected to conventional biochemical purification methods, including but not limited to affinity chromatography using an antibody specific for an epitope of the protein.

Having now generally described the invention, the same will be more readily understood through reference to the following examples which are provided by way of illustration, and are not intended to be limiting of the present invention, unless specified.

EXAMPLES

Plant Material

Rosa (rose) plants grown and maintained in a greenhouse were used to clone the cDNA corresponding to ACC synthase genes. Flower tissue in the form of senescing flower petals (from different stages) were collected in liquid nitrogen and used immediately or stored at −70° C. until use.

Messenger RNA (mRNA) Isolation

The quality of the mRNA largely determines the quality of cDNA library generated subsequently for cDNA cloning of ACC synthase genes. By "quality of the mRNA" is intended the presence of all the desired mRNA species, especially those mRNA molecules that are present in cells in relatively low abundance (either because of the number of gene copies, the rate of transcription or the stability of the mRNA). The most widely used method for preparation of RNA utilizes extraction with 4 M guanidine thiocyanate of total RNA (Chomczynski, P., et al. (1987), *Anal. Biochem.*. 162:156–159). When this method was tried by the present inventor for a geranium, the quality of RNA obtained was inadequate and did not permit a generation of a useable, high quality cDNA library (containing cDNA inserts corresponding to the least abundant mRNAs). Thus, when cDNA libraries prepared using the conventional method were screened for the presence of cDNA inserts encoding ACC synthase, the clones identified contained only partial genes or, mostly frequently, false positives. This problem alone made the process of isolating the ACC synthase genes of this invention extremely difficult and challenging. This conclusion was also suggested from the results of expression screening of such libraries with antibodies specific for the ACC synthase protein. In sum, the prior art RNA isolation technique at best invited experiments to try to find the full length genes, but provided no reasonable expectation of success. Problems posed by the poor quality of the total RNA prepared using conventional methods led the present inventor to look for alternative means for obtaining RNA of sufficiently high quality to be useful for the purposes of this invention, namely preparation of a cDNA library having a high probability of including a full length DNA sequences corresponding to low-abundance mRNAs, in particular full-length ACC synthase coding sequences.

Preparation of RNA

The preferred method discovered by the present inventor was based on the precipitation of RNA from a tissue extract using 2-butoxyethanol (Manning, K., 1991, *Anal. Biochem.* 195:45–50) with modifications. This method is referred to herein as "a 2-butoxyethanol precipitation technique." This technique was originally developed for RNA isolation, and by adapting it for mRNA isolation, the extraordinary results of this invention were achieved. Generally, in order to achieve the required RNA precipitation, a co-precipitation critical mass of RNA must be present in the preparation. The relative low proportion of RNA in relation to the total extracted material required the recognition by the present inventor that the standard amount of tissue extract used in RNA preparation, about 1 gram or less, would be insufficient for certain types of plants such as roses (discussed more fully below). The success described herein was ultimately attained by using an unusually large amount of tissue. For effort with roses, this was about 3–5 grams. While, in hindsight, this may seem like a simple problem and solution, in fact, this problem does not appear to have been considered by others, and, therefore, the novel method is not an obvious modification of the older technique.

This problem in part stems from the fact that the desired precipitation is "non-linear," meaning that no simple linear relationship exists between the mass of RNA and the amount of precipitation. Rather, the process is a threshold phenomenon, and unless that critical mass is present, precipitation will not occur. For these reasons, the prior art technique would appear on its face to be inapplicable for obtaining a high quality mRNA preparation from woody plants such as geraniums or roses. Surpassing such a critical amount of RNA, that is, an amount at which precipitation occurs, permitted the method, as modified, to demonstrate its full utility. Hence, the present inventor achieved an unexpected and extraordinary result, in spite of the fact that the technology underlying the modifications introduced to earlier methods had been available. Those of ordinary skill in the art may have appreciated (although this is not evident) that a key impediment was in the obtaining of high quality mRNA to generate a fully representative cDNA library. Furthermore, a long felt need in the art for such a library had not been satisfied. Nevertheless, substantial attempts in the prior art failed because practitioners did not understand the true nature of the reasons for failure of this type of technique.

The present inventor's discovery of a means to here achieve the co-precipitation critical mass of RNA is particularly important to the class of plants which have a low proportion of RNA in their tissue, such as less than only $1/10,000$th of the total tissue usually obtained. It is also particularly important for woody plants such as geraniums or roses, for which the present invention is particularly useful. These groups of plants comprises plant species that have a low proportion of RNA in their tissue relative to non-nucleic acid material. This is in contrast to other plants which have a higher proportion of RNA and are amenable to the preparation of high quality mRNA (and cDNA corresponding thereto) by the traditional approaches of the prior art. While this "low RNA" group of plants is known to include at least Pelargonium and Rosa (rose) species, it is clear that other plants also fall in this category, as would be evident to those skilled in the art. This group of plants is characterized in one manner as being woody (that is, they contain large amounts of fiberous material) and therefore having a low relative abundance of RNA, or conversely, as a high relative proportion of non-nucleic acid material. Thus, in this category of low RNA plants, it would be necessary to use a "large" amount of tissue, namely, an amount which (depending upon the particular plant or technique) is sufficient to yield a co-precipitant critical mass of total RNA in the process. For Pelargonium and Rosa, and the like, a co-precipitant critical mass of RNA is about 200 µg for successful implementation of the 2-butoxyethanol precipitation technique described herein. (Other RNA isolation techniques or plants may, of course, each have their own critical mass, that is, the presence of enough total RNA for precipitation to actually occur.) Thus, for the present technique and plants, about 3–5 grams of flower tissue was used initially. This may represent a minimum amount for some plants. Naturally more would also work.

The flower tissue was ground into a powder using a pestle and mortar precooled by liquid nitrogen. The resulting material was then ground with 12–20 ml of extraction buffer (0.2M boric acid/Tris-HCl and 10 mM EDTA (pH 7.6)), followed by addition of 0.24–0.4 ml of 25% sodium dodecyl sulfate (SDS) and 0.24–0.4 ml of 2-mercaptoethanol (2-ME).

The mixture was brought to room temperature and extracted with an equal volume of extraction buffer, saturated phenol/chloroform mixture. The mixture was centrifuged at 20,000×g at room temperature. The upper aqueous phase was collected and kept in a fresh tube. The interphase and lower organic phase were re-extracted with an equal volume of extraction buffer containing SDS and 2-ME. After centrifugation at 20,000×g, the second aqueous phase was removed and combined with the first aqueous phase. The pooled aqueous phase was diluted with 2.5 volume of water and a quantity of 1M sodium acetate (pH 4.5) sufficient to make the final concentration 80 mM.

This was followed by addition of 0.4 volumes of 2-butoxyethanol (2-BE). After 30 minutes on ice, the mixture was centrifuged at 20,000×g for 10 minutes at 0° C. The clear supernatant was collected. Additional 2-BE was added to bring the total to one volume. After 30 minutes on ice, the nucleic acid-containing pellet was collected by centrifugation at 20,000×g for 10 minutes at 0° C. The pellet was washed first with a 1:1 (v/v) mixture of extraction buffer and 2-BE, followed by 70% ethanol containing 0.1M potassium acetate (pH 6.0), and finally with 100% ethanol. The pellet was then air dried.

The nucleic acid pellet was dissolved in water to a concentration of about 1 mg/ml and sufficient 12M LiCl was added to bring the LiCl concentration to 3M. After one hour on ice, an RNA precipitate was collected by centrifugation at 12,000×g for 10 minutes at 0° C. The pellet was washed twice with 3M LiCl and once with 70% ethanol and was finally air dried. RNA was dissolved 0.2–0.5 ml of 10 mM Tris-HCl, 1 mM EDTA (pH 8.0) (TE buffer).

Isolation of mRNA

PolyA+mRNA was isolated by binding to Dynabeads-oligo(dT)25 (Dynal, Inc., Lake Success, N.Y.). The oligo (dT)25 is a preferred binding partner, in addition others are known in the art, the key function being merely the ability to selectively attach to the mRNA. For this binding partner, the protocol provided by the manufacturer was used. PolyA+ RNA was bound to Dynabeads in the presence of 1× binding buffer for 30 minutes. The Dynabeads serve as one of the many possible solid phase supports or carriers. This served to immobilize the mRNA. The beads were washed three times with washing buffer containing lithium dodecyl sulfate (LiDS) and once with wash buffer alone. mRNA was eluted from the beads with 50 µl of TE buffer.

The composition of the buffers was as follows:

(a) 1× Binding Buffer: 10 mM Tris-HCl (pH 7.5), 0.5M LiCl, 1 mM EDTA, 0.5% LiDS;

(b) Washing Buffer with LiDS: 10 mM Tris-HCl, 0.15M LiCl, 1 mM EDTA, 0.1% LiDS

Synthesis of cDNA

Figure 2:
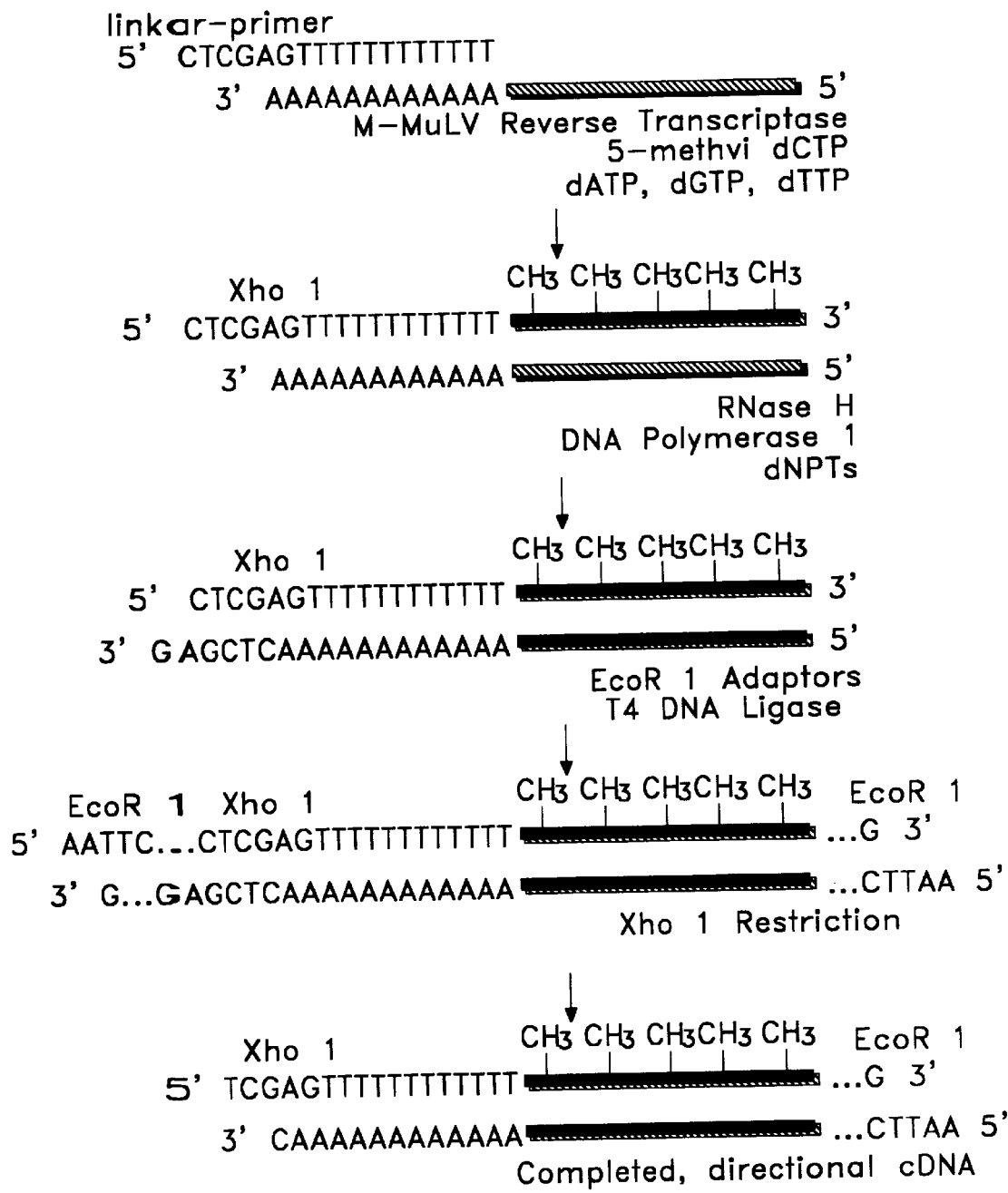
FIG. 2 is a diagram showing the details of steps of cDNA synthesis from mRNA.

The mRNA preparation (5 µg) isolated as above was used to synthesize cDNA using the ZAP Express® cDNA synthesis system from Stratagene (La Jolla, Calif.). The details of the steps of synthesis are presented in FIG. 2. The first strand synthesis was carried out with murine-Moloney leukemia virus reverse transcriptase (M-MuLV-RT) in the presence of mRNA, a primer containing a 50 base long oligonucleotide Stratagene. The unamplified cDNA library generated in this way was used for subsequent screening for ACC synthase genes.

Development of a Polymerase Chain Reaction (PCR) Probe for the Screening of ACC Synthase Genes.

The first strand of cDNA synthesis was carried out with 2 µg of mRNA using the ready-to-go T-Primed First-Strand synthesis protocol obtained from Pharmacia Biotechnology (Piscataway, N.J.). The first strand cDNA product was then used to develop a PCR probe. PCR amplification (Mullis, K. B., et al, F. A. (1987), Meth. Enzymol. 155:355–350) was performed in a Techne PHC-2 Thermocycler (Techne, Princeton, N.J.).

The following PCR primers were used for the Rose effort:

Primer I
  5'-GGIC/TTICCIGGITTC/TC/AGIG/ATIGG-3'

This is alternately designated as
  5'GGNYTNCCNGGNTTYMGNRTNGG3' (where N=inosine) [SEQ ID NO: 5]

Primer II
  5'-CAIAIICG/TG/AAAG/CC/AAICCIG/AGICC/TTC-3'

This is alternately designated as:
  5' CANANNCKRAASMANCCNRSYTC3' (where N=inosine) [SEQ ID NO: 6]

The PCR reaction (50 µl) contained 5 mM Tris-HCl (pH 8.3); 3 mM MgCl$_2$, 50 mM KCl, 50 pmol of primer I: 3 µl of synthesized first strand cDNA, 200 mM each of the four dNTPs and 25 units of- (DELTA) Taq DNA polymerase (Amersham Life Sciences, Inc., Arlington Heights, Ill.). Reaction samples were overlaid with 20 µl of mineral oil. After an initial denaturation at 95° C. for 4 minutes, samples

```
5'-GAGAGAGAGAGAGAGAGAGAACTAGTCTCGAGTTTTTTTTTTTTTTTTT-3' [SEQ ID NO: 3]
                              XhoI
``` with an XhoI restriction recognition site (shown underscored). This allows the finished cDNA to be inserted into the ZAP Express® Vector in the sense orientation (EcoRI-XhoI) with respect to the LacZ promoter. The poly (dT) region binds to the poly(A) tail of mRNA template and the reverse transcriptase starts the synthesis of first strand. The nucleotide mixture for the synthesis of first strand contained dATP, dGTP, dTTP, and 5-methyldCTP. The first strand has methyl groups on each cytosine base which protects cDNA from restriction enzymes used in subsequent cloning steps.

RNase H nicks the RNA bound to the first strand cDNA to produce multiple fragments which serve as primers for DNA polymerase I (PolI). PolI nick-translates the RNA fragments into second strand of cDNA. The cDNA ends are blunted in the presence of Klenow fragment and dNTPs. The EcoRI adaptors as shown below

```
5'AATTCGGCAGAG-3'        [SEQ ID NO: 4]
    GCCGTCTCp5'
``` are ligated to the blunt ends. The XhoI digestion of cDNA releases the EcoRI adaptor and residual linker-primer from 3'-end of the cDNA. The cDNA is size fractionated on Sephacryl-S400® and then ligated to the ZAP Express Vector® arms.

Only cDNA of 1.5 kb pairs was used to ligate into ZAP Express Vector® and then packaged into bacteriophages using Gigapack® III Gold Packaging extract protocol from were subjected to two cycles in which conditions were 94° C. for one minute for denaturation, 60° C. for two minutes for annealing; and 72° C. for one minute for extension. It was followed by 30 cycles at 94° C. for 30 seconds; 60° C. for one minute; and 72° C. for 45 seconds. The last cycle was at 72° C. for 5 minutes.

On analysis by agarose gel electrophoresis, the amplified DNA showed a DNA band of about 360 bp. The band was localized in the gel under a UV lamp and excised. DNA from the gel was purified by using Spin-Bind Recovery system from FMC BioProducts (Rockland, Me.). The DNA was then cloned using the protocol provided by manufacturer into a TA Cloning Vector called pCRII (Invitrogen, San Diego, Calif.) and then sequenced.

The 360 bp fragment cloned in the pCRII vector was excised and used to prepare a [$^{32}$P]-labeled probe. The Maga Prime system from Amersham Life Science, Inc. (Arlington Heights, Ill.) was used according to the manufacturer's protocol. The labeled DNA probe incorporated nearly 70% of the input [$\alpha^{32}$ P]dATP.

Isolation of cDNA Clones from the cDNA Library

Unamplified recombinant bacteriophages (1×10$^6$ pfu) were screened with the [$^{32}$P] labeled probe. Phages (50,000 pfu) were grown on a 150-mm NZY plate for six hours at 37° C. The plates were cooled to 4° C. Phages were transferred onto a Hybond-N+ nylon membrane (Amersham, Inc.) for 40 seconds. The DNA on membrane was denatured by treatment with 1.5 M NaCl-0.5M NaOH for 2 minutes, neutralized in 1.5M NaCl-0.5M Tris-HCl (pH 8.0) for 5 minutes and finally washed in 0.2 M Tris-HCl (pH 7.5), 2×SSC for 30 seconds. DNA was fixed onto the membrane by UV cross-linking (Strategene UV Cross-Linker) and then baked at 80° C. for one hour.

The membrane was treated with Rapid-hyb® buffer (Amersham, Inc.) at 55° C. for one hour for prehybridization and then probed with [$^{32}$P]-labeled PCR probe for 3 hours at 55° C. The membranes were washed with 2×SSC-0.1% SDS for one hour at room temperature and with 0.2-x SSC-0.1% SDS at room temperature. The filters were then exposed to X ray film (Fuji).

A total of 33 putative clones were identified during the first screening of the cDNA library. Of these putative clones, eight were further screened in the second screening cycle at lower density (1000–4000 pfu). Eight putative clones from the second screening were subjected to a tertiary screening. All these eight clones showed strong signal and were judged to be positive.

These clones were in vivo excised out of the pBK-CMV phagemid vector, and the size of the cDNA insert (representing ACC synthase genes) was determined by electrophoresis. Clones were judged to be nearly full-length, as confirmed by subsequent DNA sequencing.

DNA Sequencing of Clones

The dideoxy chain termination method (Sanger, F., et al., (1977), *Proc. Natl. Acad. Sci. USA* 74:5463–5467)) was used to sequence the ACC synthase cDNA clones for a rose. This method employed the DELTA Taq DNA polymerase protocol developed in the present inventor's laboratory (Ranu, R. S., (1995), *Biotechniques* 18:390–395) or Thermo Sequenase® (Amersham, Inc.). Based on the analysis of the DNA sequence results, the ACC synthase cDNA clones were identified as only one gene. FIG. 3 shows the various landmarks, including start codon and termination signal. The deduced amino acid sequence is shown in FIG. 4.

Several additional features of these clones and several related clones which include some noteworthy areas are described below. The clone include two stop codons on the 5' end of the untranslated region at positions 169 and 178. The regular start codon is at position 271 and the regular stop codon is at position 1711.

Development of Antibody Probes

Antibody probes were prepared for screening a cDNA expression library and for subsequent detection of ACC synthase gene products from plant cell extracts and for protein expressed from the cloned ACC synthase DNA. Based on the sequence alignment data from tomato, three peptides with largest stretches of amino acid sequence homology were selected.

(1) Peptide #1075, derived from the carboxy-terminus contained 35 amino acid residues as follows:

NVSPGSSFLCSEPGWFRVCFANMDNATLD-VALNRI                    [SEQ ID NO: 7]

(2) Peptide #1076, derived from the amino terminus contained 33 amino acids as follows:

YFDGWKAYDRDPYHSTKNSNGVIQMGLA-ENQLC                      [SEQ ID NO: 8]

(3) Peptide #1077, from the middle region contained 38 amino acid residues as follows:

YSLSKDMGMPGFRVGIIYSYNDRVVSTARR-MSSFGLVS                 [SEQ ID NO: 9]

These peptides were used to immunize rabbits. A 1:1 emulsion of 200 µg/ml of peptide in complete Freund's Adjuvant was prepared, and 0.1 ml volumes were injected subcutaneously (sc) into three different rabbits at 17 to 18 sites on the animals' backs. Before injection, a preimmune serum sample was obtained. On day 19 after the first immunization, rabbits received two intramuscular (im) injections of 0.35 ml of a 1:1 emulsion of each peptide in incomplete Freund's adjuvant at 100 µg/ml. On day 35 after the first immunization, the day 19 im protocol was repeated. On day 92, each rabbit received a booster injection (im) with the same peptide emulsion as on day 19. Seven days later, the rabbits were bled, and serum was prepared.

Western blot analysis of antisera with the three peptides showed the presence of antibodies against each of the three peptides and strong signals indicating immunization was successful. Preimmune sera were negative.

Expression of Cloned ACC Synthase Genes In Vitro

Use was made of the ZAP Express Vector system which contains a bacteriophage T$_3$ promoter. Cloned ACC synthase genes are inserted by unidirectional EcoRI/XhoI site. The cloned insert can be excised from the phage in the form of a kanamycin-resistant pBK-CMV phagemid. The digestion of the phagemid from the three ACC synthase clones described above with NotI and BamI restriction enzymes showed the absence of these restriction sites in the inserts.

DNA from clone pRoseKacc7 was prepared, linearized with NotI and used for in vitro transcription. The reaction mixture (100 µl) contained Tris-HCl (pH7.9), 40 mM; MgCl$_2$, 6 mM; DTT, 10 mM; spermidine, 2 mM; m$^7$GpppG, 1 mM; ATP, CTP and UTP, 0.5 mM each; GTP, 25 µM; Rnasin® (RNase inhibitor), 120 units; DNA template, 1–2 µg; and T$_3$ RNA polymerase, 50 units, as described in the inventor's publications. Samples were incubated at 37° C. for 20 minutes. The GTP concentration in reaction mixture was raised to 0.5 mM, and incubation was continued for one hour. Aliquots (3–5 µl) of each reaction mixture were withdrawn and subjected to agarose gel (1.2%) electrophoresis to determine the quality and efficiency of transcript synthesis. The analysis of transcript showed expected size of RNA from each clone.

The in vitro transcripts from each clone were then translated at high efficiency using rabbit reticulocyte lysates as described by the present inventor (Ranu, R. S., et al, 1979, *Meth. Enzymol.* 60:459–484) except that they were made mRNA-dependent by treatment with micrococcal ribonuclease. The in vitro translation products were immunoprecipitated with each of the three antisera described above or with a mixture of the antisera. The method used for immunoprecipitation and detection of ACC synthase protein was by Western blotting as described by the present inventor and colleagues in 1989 and recently published (Ranu, R. S., et al, (1996) *Gene Expression* 5:143–153). Translation products detected from each cloned ACC synthase gene was the size expected based on the size of the ORF of each clone. The in vitro translation product comigrate with the in vivo product upon gel electrophoresis.

Regeneration and Transformation

For the geranium, petioles from very young immature leaves from actively growing plants of *Pelargonium hortorum* cv Samba (sincerity could also have been used) were harvested and sterilized in 15% clorox for 15 minutes. They were then thoroughly rinsed with sterile distilled water (four times). The petioles were cut into 4–5 mm segments and cultured on modified MS medium as further explained in A Revised Medium For Rapid Growth And Bioassys With Tabacco Tissue Cultures, Murashige T. and Skoog, F., *Physi-* ologia Plantarum 15,473–497 (1962). Modifications consist of one half concentration of major salts and pyridoxine HCl, 1 mg/liter; nicotinic acid 1 mg/liter; and thiamine HCl 10 mg/liter. In addition, the medium used contained 5 μM BAP and 1 μM 1AA. After incubation of explants at 25° C. in the dark for three days, they were transferred to light conditions. Regeneration became apparent by 15 days and continued for five weeks. The small shoots are then subcultured individually on MS medium containing 0.44 μM BAP and 0.11 μM IAA plus 400 mg/liter of L-glutamine. After about five weeks, they developed further to about 3–4 cm long with 4–5 nodes. They were then subcultured on basal MS medium for rooting.

For transformation of geranium, pPHSacc41 was cut with Not I; the staggered ends were filled-in with dGTP and dCTP using Kelnow DNA polymerase The other end was cut with Bam HI for ligation into an agrobacterium binary vector in reverse orientation. The vector was prepared for ligation using HPA I and BamI. The ligated vector (with PHSacc41 in reverse orientation) was used to transform *Agrobacterium tumefaciens* 2760.

The petiole explants were cocultivated with agrobacterium for 5–10 minutes. After several days of cocultivation, agrobacterium cells were killed in the presence of cefotaxime (400 μg/ml) and Kananeycin (200 μg/ml). After about two weeks selection for transformants was continued. Ultimately, the transformed plants will be grown and tested for their various properties to determine which had successfully achieved the desired ACC synthase modification. The selected genetically altered plants will be used to produce a new variety or line of plants wherein the alteration is stably transmitted from generation to generation. It is anticipated that the above regeneration and transformation procedures—with some modifications as those of ordinary skill in the art would readily understand—should work for the rose application as well.

The references cited above are all incorporated by reference herein, whether specifically stated as incorporated or not. Specifically, any references mentioned in the application for this patent as well as all references listed in any information disclosure originally filed with this or the priority application are hereby incorporated by reference in their entirety to the extent such may be deemed essential to support the enablement of the invention(s), however, applicant disclaims making or supporting any statements in said references which might be considered inconsistent with the patentability of the following claims or any aspect of the invention described.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This patent covers any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims. Further, it should be understood that various permutations and combination of the elements shown in the claims (whether method or apparatus) are possible and do fall within the scope of this disclosure.

Deposits

The following illustrative plasmid encoding rose ACC synthase has been deposited at the American Type Culture Collection, Rockville, Md. under the requirements of the Budapest Treaty. This deposit has been granted the following accession number and is hereby incorporated by reference to the extent permissible:

1. pRoseKacc7 cDNA clone comprising SEQ ID NO: 1—accession number ATCC 98555.

What is claimed is:

1. An isolated DNA molecule consisting of SEQ ID NO: 1.

2. A vector useful when introduced into a rose plant cell, comprising a polynucleotide hang the nucleotide sequence of SEQ ID NO: 1, wherein the polynucleotide is inserted into the vector in reverse orientation.

3. The vector according to claim 2 which expresses an RNA having a sequence complementary to an RNA having a sequence expressed by the nucleotide sequence of SEQ ID NO: 1.

4. The vector according to claim 2 or 3 further comprising regulatory sequences required for expression of the polynucleotide.

5. The vector according to claim 4 wherein said regulatory sequences comprise a promoter active in said cell.

6. The vector according to claim 5, wherein said regulatory sequences further comprise a polyadenylation signal.

7. The vector according to claim 5, wherein said promoter is a heterologous promoter.

8. The vector according to claim 7, wherein said heterologous promoter is a viral promoter.

9. The vector according to claim 8, wherein said viral promoter is the CaMV 35S promoter.

10. The vector according to claim 7, wherein said heterologous promoter is selected from the group consisting of the SSU gene promoter, ribulose bisphosphate carboxylase promoter, chlorophyll a/b binding protein promoter, potato ST-LS1 gene promoter, soybean heat shock protein hsp17.5-E promoter, soybean heat shock protein hsp17.3-B promoter, phenylalanine ammonia-lyase promoter, petunia 5-enolpyruvylshikimate-3-phosphate synthase gene promoter, *Rhizobium meliloti* FIXD gene promoter and nopaline synthase promoter.

11. A rose cell transformed with the vector according to claim 2 or 3.

12. A mature rose plant regenerated from a cell transformed with the vector according to claim 2 or 3.

13. A transgenic part of a rose plant according to claim 12.

* * * * *

UNITED STATES PATENT AND TRADEMARK OFFICE
CERTIFICATE OF CORRECTION

PATENT NO. : 6,184,449 B1
DATED : February 6, 2001
INVENTOR(S) : Rajinder S. Ranu Page 1 of 1

It is certified that error appears in the above-identified patent and that said Letters Patent is hereby corrected as shown below:

On Title Page, Column 1, Assignee:
delete "Tagawa Greenhouses, Inc.", and add --Colorado State University through its agent Colorado State University Research Foundation (CSURF)--.

Signed and Sealed this

Seventeenth Day of July, 2001

Attest:

NICHOLAS P. GODICI
Attesting Officer
*Acting Director of the United States Patent and Trademark Office*

SEQUENCE LISTING

<160> NUMBER OF SEQ ID NOS: 9

<210> SEQ ID NO 1
<211> LENGTH: 1743
<212> TYPE: DNA
<213> ORGANISM: Rosa kardinal

<400> SEQUENCE: 1

| | | | | | |
|---|---|---|---|---|---|
| gccttggctt | tcctcccttc | gctttcttct | tcttcttctt | catcatcgta | ctctccgacg | 60 |
| acccgaaacc | ccaccgcgac | ccggcccgga | tgtctccaat | atgacccgga | cccgagacga | 120 |
| agaccggcga | cccagcagca | gcagcagcgg | cggcggagga | ggcgccgatg | agagttatag | 180 |
| tccctctaca | aggcgtggtt | caaggcagag | gaggactcgt | tctcggctcc | gtcataccat | 240 |
| gcgcgctctt | ctatttcctc | cagctttatc | atgaaacgtc | accgttccaa | ctccaacccg | 300 |
| ccgactccgc | cgccttctcc | ggactcggac | tcggaccacc | accccgccgg | gcagttggtg | 360 |
| gaagttccgg | ttctgccccg | gtcgatgtcg | aggtcccatc | tctctccgag | gaacccgggt | 420 |
| ccggtacatg | tctcgggtcg | ggccaattcg | gttttgaaag | gcggtgagcc | gccgtattat | 480 |
| gtcggcttga | ggaaggtggc | ggaggatccg | tacgacgagt | tgggtaaccc | ggatggggtt | 540 |

```
attcagctgg gtttggatga aaacaagtta gctttggact tggttcgaga ttggctactg      600
gagaatgcaa aggatgcaat actgggtggt gaggagcttg ggattagtgg gattgcttgt      660
taccagcctt ctgatggttt aatggagctc aaactggctg tggcaggatt catgtctaag      720
gccatcggaa attcagttac gtacaacccc tcacaaattg tattgacagc tggtgcaacc      780
cctgcaattg agattctaag cttctgccta gcagacagtg gaaacgcatt tctcgttccg      840
gcaccatatt accctggttt ggacagagat gtgaagtggc gaactggagt ggagataata      900
cctgttccat gccgcagtgc tgacaaattc aatttaagta taactgcact tgatcgagca      960
ttcaaccagg caaagaaacg tggtgtaaaa gttcgtggga ttataatttc aaatccttca     1020
aatcctggtg gcagtttact tactcgtgaa tcactttaca accttctgga ctttgcccga     1080
gagaagaaca ttcatataat ctcaaatgaa ttgtttgctg atccacgta tggaagtgaa      1140 gagtttgtta gcatggcaga aatcgttgat ttggaagatc tcgaccagaa cagagtgcat     1200
atagtatatg gcatatcgaa agatctctca cttccaggtt tcagggtggg tgccatctac     1260
tcctttaaca agaatgtctt gactgctgct aaaaagttga caaggttctc ttctatctcc     1320
gccccatccc aacggttgct tatctctatg ctttcagaca ccaaatttat gcataagttc     1380
atcgagatta acagagaaag gctccgtgga atgtatctta gatttgtgac aggattgaag     1440
caattgggca ttgagtgcac aaagagcaat gggggtttct actgttgggc agacttgagt     1500
gggttaattc gctcttacag tgagaaaggg gagcttgagc tctgggatag gttgttgaat     1560
gtaggtaagc tcaatgttac tcctggatct tcttgtcatt gtattgaacc gggatggttc     1620
cggttttgtt ttacgacgtt gactgaaaaa gatatccctg ttgttataga acgaattcgg     1680
aatattgccg aaacatgtaa atcacacagt tgaaatgttc gttcattcta ctcaaaaaaa     1740
aa   1743
```

<210> SEQ ID NO 2
<211> LENGTH: 480
<212> TYPE: PRT
<213> ORGANISM: Rosa kardinal

<400> SEQUENCE: 2

```
Met Lys Arg His Arg Ser Asn Ser Asn Pro Thr Pro Pro Ser
 1               5                  10                  15

Pro Asp Ser Asp Ser Asp His His Pro Ala Gly Gln Leu Val Glu Val
                20                  25                  30

Pro Val Leu Pro Arg Ser Met Ser Arg Ser His Leu Ser Pro Arg Asn
            35                  40                  45

Pro Gly Pro Val His Val Ser Gly Arg Ala Asn Ser Val Leu Lys Gly
        50                  55                  60

Gly Glu Pro Pro Tyr Tyr Val Gly Leu Arg Lys Val Ala Glu Asp Pro
65                  70                  75                  80

Tyr Asp Glu Leu Gly Asn Pro Asp Gly Val Ile Gln Leu Gly Leu Asp
                85                  90                  95

Glu Asn Lys Leu Ala Leu Asp Leu Val Arg Asp Trp Leu Glu Asn
            100                 105                 110

Ala Lys Asp Ala Ile Leu Gly Gly Glu Glu Leu Gly Ile Ser Gly Ile
        115                 120                 125

Ala Cys Tyr Gln Pro Ser Asp Gly Leu Met Glu Leu Lys Leu Ala Val
    130                 135                 140

Ala Gly Phe Met Ser Lys Ala Ile Gly Asn Ser Val Thr Tyr Asn Pro
145                 150                 155                 160
```

-continued

```
Ser Gln Ile Val Leu Thr Ala Gly Ala Thr Pro Ala Ile Glu Ile Leu
                165                 170                 175

Ser Phe Cys Leu Ala Asp Ser Gly Asn Ala Phe Leu Val Pro Ala Pro
                180                 185                 190

Tyr Tyr Pro Gly Leu Asp Arg Asp Val Lys Trp Arg Thr Gly Val Glu
                195                 200                 205

Ile Ile Pro Val Pro Cys Arg Ser Ala Asp Lys Phe Asn Leu Ser Ile
                210                 215                 220

Thr Ala Leu Asp Arg Ala Phe Asn Gln Ala Lys Lys Arg Gly Val Lys
225                 230                 235                 240

Val Arg Gly Ile Ile Ile Ser Asn Pro Ser Asn Pro Gly Gly Ser Leu
                245                 250                 255

Leu Thr Arg Glu Ser Leu Tyr Asn Leu Leu Asp Phe Ala Arg Glu Lys
                260                 265                 270

Asn Ile His Ile Ile Ser Asn Glu Leu Phe Ala Gly Ser Thr Tyr Gly
                275                 280                 285

Ser Glu Glu Phe Val Ser Met Ala Glu Ile Val Asp Leu Glu Asp Leu
                290                 295                 300

Asp Gln Asn Arg Val His Ile Val Tyr Gly Ile Ser Lys Asp Leu Ser
305                 310                 315                 320

Leu Pro Gly Phe Arg Val Gly Ala Ile Tyr Ser Phe Asn Lys Asn Val
                325                 330                 335

Leu Thr Ala Ala Lys Lys Leu Thr Arg Phe Ser Ile Ser Ala Pro
                340                 345                 350

Ser Gln Arg Leu Leu Ile Ser Met Leu Ser Asp Thr Lys Phe Met His
                355                 360                 365

Lys Phe Ile Glu Ile Asn Arg Glu Arg Leu Arg Gly Met Tyr Leu Arg
                370                 375                 380

Phe Val Thr Gly Leu Lys Gln Leu Gly Ile Glu Cys Thr Lys Ser Asn
385                 390                 395                 400

Gly Gly Phe Tyr Cys Trp Ala Asp Leu Ser Gly Leu Ile Arg Ser Tyr
                405                 410                 415

Ser Glu Lys Gly Glu Leu Glu Leu Trp Asp Arg Leu Leu Asn Val Gly
                420                 425                 430

Lys Leu Asn Val Thr Pro Gly Ser Ser Cys His Cys Ile Glu Pro Gly
                435                 440                 445

Trp Phe Arg Phe Cys Phe Thr Thr Leu Thr Glu Lys Asp Ile Pro Val
                450                 455                 460

Val Ile Glu Arg Ile Arg Asn Ile Ala Glu Thr Cys Lys Ser His Ser
465                 470                 475                 480
```

<210> SEQ ID NO 3
<211> LENGTH: 50
<212> TYPE: DNA
<213> ORGANISM: Artificial Sequence
<220> FEATURE:
<223> OTHER INFORMATION: An oligonucleotide primer with XhoI restriction site

<400> SEQUENCE: 3
gagagagaga gagagagaga actagtctcg agtttttttt tttttttttt              50

```
<210> SEQ ID NO 4
<211> LENGTH: 12
<212> TYPE: DNA
<213> ORGANISM: Artificial Sequence
<220> FEATURE:
<223> OTHER INFORMATION: EcoRI adaptor ligated to the blunt ends of cDNA

<400> SEQUENCE: 4
aattcggcag ag                                                         12

<210> SEQ ID NO 5
<211> LENGTH: 23
<212> TYPE: DNA
<213> ORGANISM: Artificial Sequence
<220> FEATURE:
<221> NAME/KEY: i
<222> LOCATION: 3, 6, 9, 12, 18, and 21
<223> OTHER INFORMATION: PCR primer

<400> SEQUENCE: 5
ggnytnccng gnttymgnrt ngg                                             23

<210> SEQ ID NO 6
<211> LENGTH: 23
<212> TYPE: DNA
<213> ORGANISM: Artificial Sequence
<220> FEATURE:
<221> NAME/KEY: i
<222> LOCATION: 3, 5, 6, 15, and 18
<223> OTHER INFORMATION: PCR primer

<400> SEQUENCE: 6
canannckra asmanccnrs ytc                                             23

<210> SEQ ID NO 7
<211> LENGTH: 35
<212> TYPE: PRT
<213> ORGANISM: Rosa kardinal

<400> SEQUENCE: 7

Asn Val Ser Pro Gly Ser Ser Phe Leu Cys Ser Glu Pro Gly Trp
 1               5                  10                  15

Phe Arg Val Cys Phe Ala Asn Met Asp Asn Ala Thr Leu Asp Val
                20                  25                  30

Ala Leu Asn Arg Ile
                35

<210> SEQ ID NO 8
<211> LENGTH: 33
<212> TYPE: PRT
<213> ORGANISM: Rosa kardinal

<400> SEQUENCE: 8

Tyr Phe Asp Gly Trp Lys Ala Tyr Asp Arg Asp Pro Tyr His Ser Thr
 1               5                  10                  15

Lys Asn Ser Asn Gly Val Ile Gln Met Gly Leu Ala Glu Asn Gln Leu
                20                  25                  30

Cys
```

```
<210> SEQ ID NO 9
<211> LENGTH: 38
<212> TYPE: PRT
<213> ORGANISM: Rosa kardinal

<400> SEQUENCE: 9

Tyr Ser Leu Ser Lys Asp Met Gly Met Pro Gly Phe Arg Val Gly Ile
1               5                   10                  15

Ile Tyr Ser Tyr Asn Asp Arg Val Val Ser Thr Ala Arg Arg Met Ser
                20                  25                  30

Ser Phe Gly Leu Val Ser
            35
```